US012667479B2

(12) United States Patent
Patel et al.

(10) Patent No.: US 12,667,479 B2
(45) Date of Patent: Jun. 30, 2026

(54) URINE OUTPUT COLLECTION AND MONITORING SYSTEMS, DEVICES, AND METHODS

(71) Applicant: C. R. Bard, Inc., Franklin Lakes, NJ (US)

(72) Inventors: Puja Patel, Lawrenceville, GA (US); Hannah Rose Kriscovich, Marietta, GA (US); Charles D. Shermer, Raleigh, NC (US); Shernone Moussignac, Conyers, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 760 days.

(21) Appl. No.: 17/863,923

(22) Filed: Jul. 13, 2022

(65) Prior Publication Data

US 2023/0025333 A1      Jan. 26, 2023

Related U.S. Application Data

(60) Provisional application No. 63/225,300, filed on Jul. 23, 2021.

(51) Int. Cl.
| | |
|---|---|
| *A61F 5/455* | (2006.01) |
| *A61B 5/145* | (2006.01) |
| *A61B 5/20* | (2006.01) |

(52) U.S. Cl.
CPC .......... *A61F 5/455* (2013.01); *A61B 5/14507* (2013.01); *A61B 5/14539* (2013.01); *A61B 5/14546* (2013.01); *A61B 5/208* (2013.01)

(58) Field of Classification Search
CPC ............ A61B 5/14507; A61B 5/14539; A61B 5/14546; A61B 5/208; A61F 5/455
See application file for complete search history.

(56) References Cited

U.S. PATENT DOCUMENTS

| | | | |
|---|---|---|---|
| 3,661,143 A | 5/1972 | Henkin | |
| 3,781,920 A | 1/1974 | Browne et al. | |
| | (Continued) | | |

FOREIGN PATENT DOCUMENTS

| | | |
|---|---|---|
| CA | 2882654 A1 | 10/2007 |
| CN | 2445749 Y | 9/2001 |
| | (Continued) | |

OTHER PUBLICATIONS

PCT/US2022/017574 filed Feb. 23, 2022 Internation Search Report and Written Opinion dated Jun. 8, 2022.

(Continued)

*Primary Examiner* — Guy K Townsend
(74) *Attorney, Agent, or Firm* — Rutan & Tucker LLP

(57) ABSTRACT

Disclosed herein are medical devices, systems, and methods for collecting urine output from a patient, generally including a urine receiving device and a collection container coupled with the urine receiving device. Collection devices described herein can automatically determine collected urine volume, and also automatically determine protein content, salt content and pH of the collected urine. Collection devices can automatically display different colors according to collected volumes of urine. Some devices can determine the volume of urine within a patient's bladder. Systems can include a bladder volume device and logic to facilitate communication with external entities. Some systems may also include a urine collection device. Urine receiving devices can include external catheters.

15 Claims, 13 Drawing Sheets

(56) References Cited

U.S. PATENT DOCUMENTS

| | | | |
|---|---|---|---|
| 3,851,650 A | 12/1974 | Darling | |
| 3,919,455 A | 11/1975 | Sigdell et al. | |
| 4,276,889 A | 7/1981 | Kuntz et al. | |
| 4,286,590 A | 9/1981 | Murase | |
| 4,291,692 A | 9/1981 | Bowman et al. | |
| 4,296,749 A | 10/1981 | Pontifex | |
| 4,305,405 A | 12/1981 | Meisch | |
| 4,312,352 A | 1/1982 | Meisch et al. | |
| 4,343,316 A | 8/1982 | Jespersen | |
| 4,443,219 A | 4/1984 | Meisch et al. | |
| 4,448,207 A | 5/1984 | Parrish | |
| 4,509,366 A | 4/1985 | Matsushita et al. | |
| 4,532,936 A | 8/1985 | LeVeen et al. | |
| 4,658,834 A | 4/1987 | Blankenship et al. | |
| 4,712,567 A | 12/1987 | Gille et al. | |
| 4,723,950 A | 2/1988 | Lee | |
| 4,763,739 A | 8/1988 | Kasinoff | |
| 4,834,706 A | 5/1989 | Beck et al. | |
| 4,850,375 A | 7/1989 | Rosenberg | |
| 4,889,532 A | 12/1989 | Metz et al. | |
| 5,002,541 A | 3/1991 | Conkling et al. | |
| 5,146,637 A | 9/1992 | Bressler et al. | |
| 5,409,014 A | 4/1995 | Napoli et al. | |
| 5,586,085 A | 12/1996 | Lichte | |
| 5,725,515 A | 3/1998 | Propp | |
| 5,733,319 A | 3/1998 | Neilson et al. | |
| 5,738,656 A | 4/1998 | Wagner | |
| 5,747,824 A | 5/1998 | Jung et al. | |
| 5,769,087 A | 6/1998 | Westphal et al. | |
| 5,807,278 A | 9/1998 | McRae | |
| 5,823,972 A | 10/1998 | McRae | |
| 5,891,051 A | 4/1999 | Han et al. | |
| 5,911,786 A | 6/1999 | Nielsen et al. | |
| 6,129,684 A | 10/2000 | Sippel et al. | |
| 6,132,407 A | 10/2000 | Genese et al. | |
| 6,250,152 B1 | 6/2001 | Klein et al. | |
| 6,256,532 B1 | 7/2001 | Cha | |
| 6,261,254 B1 | 7/2001 | Baron et al. | |
| 6,434,418 B1 | 8/2002 | Neal et al. | |
| 6,454,372 B1 | 9/2002 | Yang | |
| 6,579,247 B1 | 6/2003 | Abramovitch et al. | |
| 6,592,612 B1 | 7/2003 | Samson et al. | |
| 6,709,420 B1 | 3/2004 | Lincoln et al. | |
| 6,716,200 B2 | 4/2004 | Bracken et al. | |
| 7,011,634 B2 | 3/2006 | Paasch et al. | |
| 7,161,484 B2 | 1/2007 | Tsoukalis | |
| 7,211,037 B2 | 5/2007 | Briggs et al. | |
| 7,437,945 B1 | 10/2008 | Feller | |
| 7,442,754 B2 | 10/2008 | Tepper et al. | |
| 7,739,907 B2 | 6/2010 | Boiarski | |
| 7,871,385 B2 | 1/2011 | Levinson | |
| 7,931,630 B2 | 4/2011 | Nishtala et al. | |
| 7,976,533 B2 | 7/2011 | Larsson | |
| 7,998,126 B1 | 8/2011 | Fernandez | |
| 8,295,933 B2 | 10/2012 | Gerber et al. | |
| 8,328,733 B2 | 12/2012 | Forte et al. | |
| 8,328,734 B2 | 12/2012 | Salvadori et al. | |
| 8,337,476 B2 * | 12/2012 | Greenwald | A61B 10/007 |
| | | | 73/216 |
| 8,374,688 B2 | 2/2013 | Libbus et al. | |
| 8,403,884 B2 | 3/2013 | Nishtala | |
| 8,471,231 B2 | 6/2013 | Paz | |
| 8,663,128 B2 | 3/2014 | Paz et al. | |
| 8,773,259 B2 | 7/2014 | Judy et al. | |
| 8,790,277 B2 | 7/2014 | Elliott et al. | |
| 8,790,320 B2 | 7/2014 | Christensen | |
| 8,790,577 B2 | 7/2014 | Mizumoto et al. | |
| 8,813,551 B2 | 8/2014 | Boiarski | |
| 8,827,924 B2 | 9/2014 | Paz et al. | |
| 8,832,558 B2 | 9/2014 | Cardarelli et al. | |
| 8,900,196 B2 | 12/2014 | Andino | |
| 9,045,887 B2 | 6/2015 | O'Malley | |
| 9,050,046 B2 | 6/2015 | Elliott et al. | |
| 9,074,920 B2 | 7/2015 | Mendels et al. | |
| 9,216,242 B2 | 12/2015 | Nishtala et al. | |
| 9,480,821 B2 | 11/2016 | Ciccone et al. | |
| 9,592,034 B2 | 3/2017 | Hall et al. | |
| 9,642,987 B2 | 5/2017 | Bierman et al. | |
| 9,731,097 B2 | 8/2017 | Andino et al. | |
| 9,895,095 B2 | 2/2018 | Chen | |
| 9,928,341 B2 * | 3/2018 | Angelides | G16H 40/67 |
| 9,962,516 B2 | 5/2018 | Lampotang et al. | |
| 10,071,202 B2 | 9/2018 | Handler | |
| 10,182,747 B2 | 1/2019 | Charlez et al. | |
| 10,245,008 B2 | 4/2019 | Paige | |
| 10,301,807 B1 | 5/2019 | Kolesar | |
| 10,362,981 B2 | 7/2019 | Paz et al. | |
| 10,383,606 B1 | 8/2019 | McCord et al. | |
| 10,448,875 B2 * | 10/2019 | Holt | G01F 23/268 |
| 10,722,679 B2 | 7/2020 | Lampotang et al. | |
| 10,799,386 B1 | 10/2020 | Harrison, Sr. | |
| 10,881,320 B2 * | 1/2021 | Duval | A61B 5/4233 |
| 10,881,778 B2 | 1/2021 | Scarpaci et al. | |
| 11,291,577 B2 * | 4/2022 | Seres | A61F 5/4404 |
| 11,473,958 B2 * | 10/2022 | Holt | G01F 1/56 |
| 11,540,760 B1 | 1/2023 | Guillemette | |
| 11,654,042 B2 | 5/2023 | Hughett, Sr. | |
| 11,703,365 B2 | 7/2023 | Tourchak et al. | |
| 12,083,261 B2 * | 9/2024 | Justice | A61M 1/73 |
| 12,109,353 B2 | 10/2024 | Cheng et al. | |
| 12,364,423 B2 | 7/2025 | Cheng et al. | |
| 12,408,853 B2 * | 9/2025 | Kriscovich | A61B 5/208 |
| 2001/0056226 A1 | 12/2001 | Zodnik et al. | |
| 2002/0013518 A1 | 1/2002 | West et al. | |
| 2002/0016719 A1 | 2/2002 | Nemeth et al. | |
| 2002/0161314 A1 | 10/2002 | Sarajarvi | |
| 2002/0193760 A1 | 12/2002 | Thompson | |
| 2003/0000303 A1 | 1/2003 | Livingston et al. | |
| 2003/0163183 A1 | 8/2003 | Carson | |
| 2003/0163287 A1 | 8/2003 | Vock et al. | |
| 2004/0267086 A1 | 12/2004 | Anstadt et al. | |
| 2005/0020958 A1 | 1/2005 | Paolini et al. | |
| 2005/0065583 A1 | 3/2005 | Voorhees et al. | |
| 2005/0172712 A1 | 8/2005 | Nyce | |
| 2005/0247121 A1 | 11/2005 | Pelster | |
| 2006/0065713 A1 | 3/2006 | Kingery | |
| 2006/0100743 A1 | 5/2006 | Townsend et al. | |
| 2006/0253091 A1 | 11/2006 | Vernon | |
| 2007/0010797 A1 | 1/2007 | Nishtala et al. | |
| 2007/0078444 A1 | 4/2007 | Larsson | |
| 2007/0106177 A1 | 5/2007 | Hama | |
| 2007/0145137 A1 | 6/2007 | Mrowiec | |
| 2007/0225668 A1 | 9/2007 | Otto | |
| 2007/0252714 A1 | 11/2007 | Rondoni et al. | |
| 2008/0027409 A1 | 1/2008 | Rudko et al. | |
| 2008/0217391 A1 | 9/2008 | Roof et al. | |
| 2008/0312550 A1 | 12/2008 | Nishtala et al. | |
| 2008/0312556 A1 | 12/2008 | Dijkman | |
| 2009/0056020 A1 | 3/2009 | Caminade et al. | |
| 2009/0099629 A1 | 4/2009 | Carson et al. | |
| 2009/0157430 A1 | 6/2009 | Rule et al. | |
| 2009/0171169 A1 | 7/2009 | Nagata | |
| 2009/0287170 A1 | 11/2009 | Otto | |
| 2009/0315684 A1 | 12/2009 | Sacco et al. | |
| 2010/0064426 A1 | 3/2010 | Chikara Imamura | |
| 2010/0094204 A1 | 4/2010 | Nishtala | |
| 2010/0122963 A1 | 5/2010 | Costa et al. | |
| 2010/0130949 A1 | 5/2010 | Garcia | |
| 2010/0137743 A1 | 6/2010 | Nishtala et al. | |
| 2010/0262047 A1 | 10/2010 | Genis | |
| 2011/0113540 A1 | 5/2011 | Plate et al. | |
| 2011/0120219 A1 | 5/2011 | Barlesi et al. | |
| 2011/0178425 A1 | 7/2011 | Nishtala et al. | |
| 2011/0224636 A1 | 9/2011 | Keisic | |
| 2011/0230824 A1 | 9/2011 | Salinas et al. | |
| 2011/0238042 A1 | 9/2011 | Davis et al. | |
| 2011/0251572 A1 | 10/2011 | Nishtala et al. | |
| 2011/0263952 A1 | 10/2011 | Bergman et al. | |
| 2012/0029408 A1 | 2/2012 | Beaudin | |
| 2012/0035496 A1 | 2/2012 | Denison et al. | |
| 2012/0059286 A1 | 3/2012 | Hastings et al. | |
| 2012/0078137 A1 | 3/2012 | Mendels et al. | |
| 2012/0078235 A1 | 3/2012 | Martin et al. | |
| 2012/0095304 A1 | 4/2012 | Biondi | |

(56)  References Cited

U.S. PATENT DOCUMENTS

| | | |
|---|---|---|
| 2012/0108917 A1 | 5/2012 | Libbus et al. |
| 2012/0109008 A1 | 5/2012 | Charlez et al. |
| 2012/0118650 A1 | 5/2012 | Gill |
| 2012/0123233 A1 | 5/2012 | Cohen |
| 2012/0127103 A1 | 5/2012 | Qualey et al. |
| 2012/0226196 A1 | 9/2012 | DiMino et al. |
| 2012/0234434 A1 | 9/2012 | Woodruff et al. |
| 2012/0302917 A1 | 11/2012 | Fitzgerald et al. |
| 2012/0323144 A1 | 12/2012 | Coston et al. |
| 2012/0323502 A1 | 12/2012 | Tanoura et al. |
| 2013/0066166 A1 | 3/2013 | Burnett et al. |
| 2013/0109927 A1 | 5/2013 | Menzel |
| 2013/0109928 A1 | 5/2013 | Menzel |
| 2013/0131610 A1 | 5/2013 | Dewaele et al. |
| 2013/0218106 A1 | 8/2013 | Coston et al. |
| 2013/0245498 A1 | 9/2013 | Delaney et al. |
| 2013/0267871 A1 | 10/2013 | Delaney et al. |
| 2014/0039348 A1 | 2/2014 | Bullington et al. |
| 2014/0155781 A1 | 6/2014 | Bullington et al. |
| 2014/0155782 A1 | 6/2014 | Bullington et al. |
| 2014/0159921 A1 | 6/2014 | Qualey et al. |
| 2014/0166691 A1 | 6/2014 | Chen et al. |
| 2014/0187666 A1 | 7/2014 | Aizenberg et al. |
| 2014/0207085 A1 | 7/2014 | Brandt et al. |
| 2014/0243635 A1 | 8/2014 | Arefieg |
| 2014/0335490 A1 | 11/2014 | Baarman et al. |
| 2015/0120321 A1 | 4/2015 | David et al. |
| 2015/0233749 A1 | 8/2015 | Wang et al. |
| 2015/0342576 A1 | 12/2015 | Hall et al. |
| 2015/0343173 A1 | 12/2015 | Tobescu et al. |
| 2015/0359522 A1 | 12/2015 | Recht et al. |
| 2015/0362351 A1 | 12/2015 | Joshi et al. |
| 2016/0051176 A1 | 2/2016 | Ramos et al. |
| 2016/0051177 A1 | 2/2016 | Chen |
| 2016/0183819 A1 | 6/2016 | Burnett et al. |
| 2016/0374874 A1 | 12/2016 | Trepanier et al. |
| 2017/0035342 A1 | 2/2017 | Elia et al. |
| 2017/0043089 A1 | 2/2017 | Handler |
| 2017/0100068 A1 | 4/2017 | Kostov |
| 2017/0113000 A1 | 4/2017 | Tobescu et al. |
| 2017/0136209 A1 | 5/2017 | Burnett et al. |
| 2017/0140103 A1 | 5/2017 | Angelides |
| 2017/0196478 A1 | 7/2017 | Hunter |
| 2017/0202698 A1 | 7/2017 | Zani et al. |
| 2017/0241978 A1 | 8/2017 | Duval |
| 2017/0249445 A1 | 8/2017 | Devries et al. |
| 2017/0290540 A1 | 10/2017 | Franco |
| 2017/0291012 A1 | 10/2017 | Iglesias |
| 2017/0307423 A1 | 10/2017 | Pahwa et al. |
| 2017/0322197 A1 | 11/2017 | Hall et al. |
| 2018/0015251 A1 | 1/2018 | Lampotang et al. |
| 2018/0110455 A1 | 4/2018 | Chang et al. |
| 2018/0110456 A1 | 4/2018 | Cooper et al. |
| 2018/0160961 A1 | 6/2018 | Gopinathan et al. |
| 2018/0214122 A1 | 8/2018 | Ansell et al. |
| 2018/0214297 A1 | 8/2018 | Hughett et al. |
| 2018/0245967 A1 | 8/2018 | Parker et al. |
| 2018/0280236 A1 | 10/2018 | Ludin et al. |
| 2018/0306661 A1 | 10/2018 | Stacey |
| 2018/0317891 A1 | 11/2018 | Kim |
| 2018/0344234 A1 | 12/2018 | McKinney et al. |
| 2019/0006047 A1 | 1/2019 | Gorek et al. |
| 2019/0017535 A1 | 1/2019 | Ormsbee et al. |
| 2019/0046102 A1 | 2/2019 | Kushnir et al. |
| 2019/0069829 A1 | 3/2019 | Bulut |
| 2019/0069830 A1 | 3/2019 | Holt et al. |
| 2019/0126006 A1 | 5/2019 | Rehm et al. |
| 2019/0150821 A1 | 5/2019 | Waters et al. |
| 2019/0167144 A1 | 6/2019 | Jung et al. |
| 2019/0201596 A1 | 7/2019 | Luxon et al. |
| 2019/0218826 A1 | 7/2019 | Allen et al. |
| 2019/0223844 A1 | 7/2019 | Aboagye et al. |
| 2019/0231244 A1 | 8/2019 | Swan et al. |
| 2019/0247236 A1 | 8/2019 | Sides et al. |
| 2019/0254582 A1 | 8/2019 | Wei et al. |
| 2019/0298317 A1* | 10/2019 | Colgan .................. A61B 5/207 |
| 2019/0321588 A1 | 10/2019 | Burnett et al. |
| 2019/0328945 A1 | 10/2019 | Analytis et al. |
| 2019/0343445 A1 | 11/2019 | Burnett et al. |
| 2019/0358387 A1* | 11/2019 | Elbadry ................. G01N 15/06 |
| 2019/0365308 A1 | 12/2019 | Laing et al. |
| 2019/0381223 A1 | 12/2019 | Culbert et al. |
| 2020/0022637 A1 | 1/2020 | Kurzrock et al. |
| 2020/0064172 A1* | 2/2020 | Tabaczewski ......... A61B 5/201 |
| 2020/0085378 A1 | 3/2020 | Burnett et al. |
| 2020/0121300 A1 | 4/2020 | Moore |
| 2020/0187863 A1 | 6/2020 | Tu et al. |
| 2020/0268302 A1 | 8/2020 | Oh |
| 2020/0268303 A1 | 8/2020 | Oliva |
| 2020/0289749 A1 | 9/2020 | Odashima et al. |
| 2020/0405524 A1 | 12/2020 | Gill |
| 2021/0054610 A1 | 2/2021 | Hall et al. |
| 2021/0077007 A1 | 3/2021 | Jouret et al. |
| 2021/0098124 A1 | 4/2021 | Crook et al. |
| 2021/0100533 A1* | 4/2021 | Seres ...................... A61B 5/42 |
| 2021/0113130 A1* | 4/2021 | Tran ................... A61B 5/14532 |
| 2021/0202084 A1 | 7/2021 | Cronin et al. |
| 2021/0298653 A1 | 9/2021 | Woodard et al. |
| 2021/0299353 A1 | 9/2021 | Mannu et al. |
| 2021/0361211 A1 | 11/2021 | Teramoto et al. |
| 2022/0018692 A1 | 1/2022 | Tourchak et al. |
| 2022/0026001 A1 | 1/2022 | Cheng et al. |
| 2022/0026261 A1 | 1/2022 | Funnell et al. |
| 2022/0079487 A1 | 3/2022 | Horiguchi et al. |
| 2022/0192564 A1* | 6/2022 | Kriscovich ............ A61B 5/208 |
| 2022/0192565 A1 | 6/2022 | Cheng et al. |
| 2022/0192566 A1 | 6/2022 | Cheng et al. |
| 2022/0193375 A1 | 6/2022 | Rehm et al. |
| 2022/0233120 A1 | 7/2022 | Beuret et al. |
| 2022/0296140 A1 | 9/2022 | Nguyen et al. |
| 2022/0330867 A1 | 10/2022 | Conley et al. |
| 2022/0386917 A1 | 12/2022 | Mann et al. |
| 2023/0019703 A1 | 1/2023 | Behzad et al. |
| 2023/0022547 A1 | 1/2023 | Cho et al. |
| 2023/0025333 A1* | 1/2023 | Patel .................. A61B 5/14539 |
| 2023/0028966 A1 | 1/2023 | Franano |
| 2023/0035669 A1 | 2/2023 | Raja et al. |
| 2023/0040915 A1 | 2/2023 | Compton et al. |
| 2023/0058553 A1 | 2/2023 | Fallows et al. |
| 2023/0060232 A1 | 3/2023 | Patel et al. |
| 2023/0084476 A1 | 3/2023 | Robichaud et al. |
| 2023/0089041 A1 | 3/2023 | Handler |
| 2024/0042120 A1 | 2/2024 | Cheng et al. |
| 2024/0081708 A1 | 3/2024 | Kelly et al. |
| 2024/0108268 A1 | 4/2024 | Woodard et al. |
| 2024/0252783 A1 | 8/2024 | Waitkus et al. |
| 2024/0347162 A1 | 10/2024 | Meese et al. |
| 2024/0360938 A1 | 10/2024 | Cheng et al. |
| 2024/0424186 A1 | 12/2024 | Justice et al. |
| 2025/0090066 A1 | 3/2025 | Tourchak |
| 2025/0120636 A1 | 4/2025 | Compton et al. |
| 2025/0205456 A1 | 6/2025 | Rehm et al. |
| 2025/0339073 A1 | 11/2025 | Cheng et al. |
| 2026/0000330 A1 | 1/2026 | Kriscovich et al. |
| 2026/0033762 A1 | 2/2026 | Fallows et al. |

FOREIGN PATENT DOCUMENTS

| | | |
|---|---|---|
| CN | 200951235 Y | 9/2007 |
| CN | 201492414 U | 6/2010 |
| CN | 102647939 A | 8/2012 |
| CN | 103054559 B | 5/2015 |
| CN | 104921738 A | 9/2015 |
| CN | 205306875 U | 6/2016 |
| CN | 107952140 A | 4/2018 |
| CN | 109498013 A | 3/2019 |
| CN | 110859636 A | 3/2020 |
| CN | 112426156 A | 3/2021 |
| EP | 0342028 A2 | 11/1989 |
| ES | 2760470 T3 | 5/2020 |
| GB | 2437549 A | 10/2007 |
| GB | 2576743 A | 3/2020 |
| JP | S49-75171 A | 7/1974 |
| JP | S54-147066 A | 11/1979 |

(56) References Cited

FOREIGN PATENT DOCUMENTS

| | | | |
|---|---|---|---|
| JP | S58-190719 | A | 11/1983 |
| JP | S60-219517 | A | 11/1985 |
| JP | H02-057240 | B2 | 12/1990 |
| JP | H08-271301 | A | 10/1996 |
| JP | H10-104041 | A | 4/1998 |
| JP | 2007-303982 | A | 11/2007 |
| JP | 2008-524618 | A | 7/2008 |
| JP | 2009-068959 | A | 4/2009 |
| JP | 2010-121950 | A | 6/2010 |
| JP | 2010-530978 | A | 9/2010 |
| JP | 2012-105947 | A | 6/2012 |
| JP | 2012-225790 | A | 11/2012 |
| JP | 2018108356 | A | 7/2018 |
| KR | 20070115495 | A | 12/2007 |
| NL | 2013740 | A | 8/2016 |
| RU | 2615727 | C2 | 4/2017 |
| WO | 1981003427 | A1 | 12/1981 |
| WO | 2004045410 | A1 | 6/2004 |
| WO | 2013013782 | A2 | 1/2013 |
| WO | 20130178742 | A1 | 12/2013 |
| WO | 2014/043650 | A2 | 3/2014 |
| WO | 2014105755 | A1 | 7/2014 |
| WO | 2014108690 | A1 | 7/2014 |
| WO | 2014/135856 | A1 | 9/2014 |
| WO | 2014/151068 | A2 | 9/2014 |
| WO | 2014145971 | A2 | 9/2014 |
| WO | 201511402 | A1 | 1/2015 |
| WO | 2015/105916 | A1 | 7/2015 |
| WO | 2015/127390 | A1 | 8/2015 |
| WO | 2015191125 | A1 | 12/2015 |
| WO | 2016177901 | A1 | 11/2016 |
| WO | 2017/023794 | A1 | 2/2017 |
| WO | 2018156624 | A1 | 8/2018 |
| WO | 2019066357 | A1 | 4/2019 |
| WO | 2019106675 | A1 | 6/2019 |
| WO | 2019/226697 | A1 | 11/2019 |
| WO | 2020033752 | A1 | 2/2020 |
| WO | 2020154370 | A1 | 7/2020 |
| WO | 2020251893 | A1 | 12/2020 |
| WO | 2022108589 | A1 | 5/2022 |
| WO | 2022182794 | A1 | 9/2022 |
| WO | 2023022895 | A1 | 2/2023 |
| WO | 2023027871 | A1 | 3/2023 |
| WO | 2023076067 | A1 | 5/2023 |

OTHER PUBLICATIONS

Schlebusch, T. et al., "Bladder volume estimation from electrical impedance tomography" Physiological Measurement Institute of Physics Publishing, Bristol, GB. vol. 35 No. 9 Aug. 20, 2014. (Aug. 20, 2014).

U.S. Appl. No. 17/306,821, filed May 3, 2021 Final Office Action dated Jul. 19, 2023.

U.S. Appl. No. 17/556,907, filed Dec. 20, 2021 Non-Final Office Action dated Aug. 17, 2023.

U.S. Appl. No. 15/748,107, filed Jan. 26, 2018 Notice of Allowance dated Dec. 12, 2022.

U.S. Appl. No. 17/054,493, filed Nov. 10, 2020 Non-Final Office Action dated Jan. 27, 2023.

U.S. Appl. No. 17/3026,821, filed May 3, 2021 Non-Final Office Action dated Jan. 10, 2023.

U.S. Appl. No. 17/373,535, filed Jul. 12, 2021 Non-Final Office Action dated Nov. 9, 2022.

Bard Medical, Criticore Disposables—Non I.C., 3 pages, www.bardmedical.com/products/patienl-moniloring-,ystems/criticore®-system/criticore®disposables-non-ic/ Jan. 30, 2015.

Bard Medical, Criticore Infection Control Disposables, 3 pages, www.bardmedical.com/patienl-moniloring-,ystems/criticore®-system/criticore®-infection-control-disposables/ Jan. 30, 2015.

Bard Medical, Criticore Monitor, 11 pages, www.bardmedical.com/products/patient-monitoring-systems/criticore®--monitor/ Jan. 30, 2015.

Bard Medical, Urine Meiers, 3 pages, www.bardmedical.com/products/urological-drainage/urine-collection/urinemeters/ Jan. 30, 2015.

Biometrix, Urimetrix, 4 pages, www.biometrixmedical.com/Products/56/Urimetrix%E2%84%A2 Oct. 29, 2014.

Observe Medical, sippi, 3 pages, www.observemedical.com/products.html Oct. 29, 2014.

PCT/US19/33389 filed May 21, 2019 International Search Report and Written Opinion dated Aug. 2, 2019.

PCT/US2016/044835 filed Jul. 20, 2016 International Search Report and Written Opinion dated Dec. 16, 2016.

PCT/US2019/045787 filed Aug. 8, 2019 International Preliminary Report on Patentability dated Feb. 16, 2021.

PCT/US2019/045787 filed Aug. 8, 2019 International Search Report and Written Opinion dated Oct. 2, 2019.

U.S. Appl. No. 17/054,493, filed Nov. 10, 2020 Final Office Action dated May 31, 2022.

U.S. Appl. No. 15/748,107, filed Jan. 26, 2018 Final Office Action dated Dec. 23, 2020.

U.S. Appl. No. 15/748,107, filed Jan. 26, 2018 Final Office Action dated Feb. 7, 2022.

U.S. Appl. No. 15/748,107, filed Jan. 26, 2018 Non-Final Office Action dated Sep. 3, 2021.

U.S. Appl. No. 15/748,107, filed Jan. 26, 2018 Non-Final Office Action dated Sep. 4, 2020.

U.S. Appl. No. 17/054,493, filed Nov. 10, 2020 Non-Final Office Action dated Nov. 24, 2021.

DFree Personal—Consumer Product Brochure, 2019.

DFree Pro Brochure 2019.

Leonhäuser, D et al., "Evaluation of electrical impedance tomography for determination of urinary bladder volume: comparison with standard ultrasound methods in healthy volunteers."—BioMed Engr On-line; 17:95; 2018.

Li, R., et al., "Design of a Noninvasive Bladder Urinary vol. Monitoring System Based on Bio-Impedance."—Engineering; vol. 5; pp. 321-325; 2013.

Reichmuth, M., et al., "A Non-invasive Wearable Bioimpedance System to Wirelessly Monitor Bladder Filling."—Dep. of Health Sciences and Technology—Department of Information Technology and Electrical Engineering ETH Zurich, Zurich, Switzerland—Conference Paper; Mar. 2020.

SECA product catalog, https://US.secashop.com/products/seca-mbca/seca-mbca-514/5141321139, last accessed Sep. 11, 2020.

U.S. Appl. No. 17/054,493, filed Nov. 10, 2020 Final Office Action dated Oct. 4, 2023.

U.S. Appl. No. 17/262,080, filed Jan. 21, 2021 Final Office Action dated Sep. 11, 2023.

U.S. Appl. No. 17/262,080, filed Jan. 21, 2021 Notice of Allowance dated Oct. 13, 2023.

U.S. Appl. No. 17/306,821, filed May 3, 2021 Advisory Action dated Oct. 3, 2023.

U.S. Appl. No. 17/373,546, filed Jul. 12, 2021 Non-Final Office Action dated Nov. 1, 2023.

"Volumetric Flow Rate", www.vcalc.com/wiki/JeffNolumetric+%28Fluid%29+Flow+Rate, accessed Jan. 9, 2025, created Mar. 8, 2018 (Year: 2018).

U.S. Appl. No. 17/552,250, filed Dec. 15, 2021 Final Office Action dated Feb. 11, 2025.

U.S. Appl. No. 17/556,931, filed Dec. 20, 2021 Advisory Action dated Dec. 6, 2024.

U.S. Appl. No. 17/556,931, filed Dec. 20, 2021 Notice of Allowance dated Mar. 18, 2025.

U.S. Appl. No. 17/587,938, filed Jan. 28, 2022 Restriction Requirement dated Jan. 22, 2025.

U.S. Appl. No. 17/682,785, filed Feb. 28, 2022 Restriction Requirement dated Apr. 2, 2025.

U.S. Appl. No. 17/833,682, filed Jun. 6, 2022 Non-Final Office Action dated Jan. 15, 2025.

U.S. Appl. No. 17/863,223, filed Jul. 12, 2022 Non-Final Office Action dated Apr. 2, 2025.

U.S. Appl. No. 17/870,698, filed Jul. 21, 2022 Restriction Requirement dated Feb. 12, 2025.

(56) References Cited

OTHER PUBLICATIONS

U.S. Appl. No. 17/879,658, filed Aug. 2, 2022 Non-Final Office Action dated Dec. 30, 2024.

U.S. Appl. No. 17/893,435, filed Aug. 23, 2022 Non-Final Office Action dated Jan. 17, 2025.

"Urocare Reusable Night Drain Bottle—Urinary Collection System" Aug. 13, 2020, HealthProductsForYou.com, <https://www.healthproductsforyou.com/p-urocare-reusable-night-drain-bottle-urinary-collection-system.html> retrieved from Archive.org (Year: 2020).

U.S. Appl. No. 17/552,250, filed Dec. 15, 2021 Non-Final Office Action dated Sep. 19, 2024.

U.S. Appl. No. 17/556,931, filed Dec. 20, 2021 Final Office Action dated Oct. 1, 2024.

U.S. Appl. No. 17/560,079, filed Dec. 22, 2021 Notice of Allowance dated Oct. 29, 2024.

PCT/US20/61367 filed Nov. 19, 2020 International Search Report and Written Opinion dated Feb. 22, 2021.

U.S. Appl. No. 17/262,080, filed Jan. 21, 2021 Non-Final Office Action dated Apr. 6, 2023.

U.S. Appl. No. 17/373,535, filed Jul. 12, 2021 Notice of Allowance dated Feb. 23. 2023.

U.S. Appl. No. 17/556,907, filed Dec. 20, 2021 Restriction Requirement dated May 12, 2023.

U.S. Appl. No. 17/552,250, filed Dec. 15, 2021 Advisory Action dated May 8, 2025.

U.S. Appl. No. 17/552,250, filed Dec. 15, 2021 Notice of Allowance dated May 20, 2025.

U.S. Appl. No. 17/587,938, filed Jan. 28, 2022 Non-Final Office Action dated May 12, 2025.

U.S. Appl. No. 17/682,785, filed Feb. 28, 2022 Non-Final Office Action dated Jul. 16, 2025.

U.S. Appl. No. 17/833,682, filed Jun. 6, 2022 Final Office Action dated May 12, 2025.

U.S. Appl. No. 17/870,698, filed Jul. 21, 2022 Non-Final Office Action dated Apr. 9, 2025.

U.S. Appl. No. 17/873,834, filed Jul. 26, 2022 Non-Final Office Action dated May 19, 2025.

U.S. Appl. No. 17/879,658, filed Aug. 2, 2022 Final Office Action dated May 14, 2025.

U.S. Appl. No. 17/883,507, filed Aug. 8, 2022 Restriction Requirement dated May 19, 2025.

U.S. Appl. No. 17/893,435, filed Aug. 23, 2022 Notice of Allowance dated Jul. 11, 2025.

U.S. Appl. No. 17/941,941, filed Sep. 9, 2022 Restriction Requirement dated May 28, 2025.

U.S. Appl. No. 18/036,335, filed May 10, 2023 Non-Final Office Action dated Jun. 18, 2025.

U.S. Appl. No. 18/278,167, filed Aug. 21, 2023 Non-Final Office Action dated Apr. 24, 2025.

U.S. Appl. No. 18/682,075, filed Feb. 7, 2024 Non-Final Office Action dated Jun. 18, 2025.

EP 20962628.2 filed May 31, 2023 Extended European Search Report dated Apr. 20, 2024.

EP 23188337.2 filed May 21, 2019 Extended European Search Report dated Dec. 4, 2023.

PCT/US2019/033389 filed Nov. 26, 2020 Extended European Search Report dated Jun. 4, 2021.

PCT/US2022/039191 filed Aug. 2, 2022 International Search Report and Written Opinion dated Dec. 5, 2022.

PCT/US2022/039746 filed Aug. 8, 2022 International Search Report and Written Opinion dated Nov. 18, 2022.

PCT/US2022/046920 filed Oct. 17, 2022 International Search Report and Written Opinion dated Feb. 20, 2023.

U.S. Appl. No. 17/054,493, filed Nov. 10, 2020 Notice of Allowance dated Jan. 4, 2024.

U.S. Appl. No. 17/306,821, filed May 3, 2021 Notice of Allowance dated Apr. 23, 2024.

U.S. Appl. No. 17/373,546, filed Jul. 12, 2021 Notice of Allowance dated Mar. 7, 2024.

U.S. Appl. No. 17/373,546, filed Jul. 12, 2021 Notice of Allowance dated May 29, 2024.

U.S. Appl. No. 17/556,907, filed Dec. 20, 2021 Notice of Allowance dated Dec. 6, 2023.

U.S. Appl. No. 17/556,931, filed Dec. 20, 2021 Non-Final Office Action dated Mar. 27, 2024.

U.S. Appl. No. 17/556,931, filed Dec. 20, 2021 Restriction Requirement dated Feb. 22, 2024.

U.S. Appl. No. 17/682,785, filed Feb. 28, 2022 Final Office Action dated Jan. 9, 2026.

U.S. Appl. No. 17/833,682, filed Jun. 6, 2022 Final Office Action dated Jan. 16, 2026.

U.S. Appl. No. 17/863,223, filed Jul. 12, 2022 Advisory Action dated Dec. 1, 2025.

U.S. Appl. No. 17/870,698, filed Jul. 21, 2022 Non-Final Office Action dated Nov. 21, 2025.

U.S. Appl. No. 17/873,834, filed Jul. 26, 2022 Final Office Action dated Nov. 28, 2025.

U.S. Appl. No. 17/879,658, filed Aug. 2, 2022 Non-Final Office Action dated Nov. 18, 2025.

U.S. Appl. No. 18/036,335, filed May 10, 2023 Notice of Allowance dated Oct. 21, 2025.

U.S. Appl. No. 17/833,682, filed Jun. 6, 2022 Non-Final Office Action dated Sep. 15, 2025.

U.S. Appl. No. 17/863,223, filed Jul. 12, 2022 Final Office Action dated Sep. 24, 2025.

U.S. Appl. No. 17/870,698, filed Jul. 21, 2022 Final Office Action dated Jul. 29, 2025.

U.S. Appl. No. 17/883,507, filed Aug. 8, 2022 Non-Final Office Action dated Aug. 27, 2025.

U.S. Appl. No. 17/941,941, filed Sep. 9, 2022 Non-Final Office Action dated Aug. 22, 2025.

U.S. Appl. No. 18/278,167, filed Aug. 21, 2023 Notice of Allowance dated Oct. 16, 2025.

Weight Module Measuring Equipment, Hopper Weighing Module, www.web.archive.org/web/20210422161926/http://modul-ves.ru/catalog/bunkernye-vesy/vesovoy-modul-dlya-bunkera/, Apr. 22, 2021, accessed Sep. 10, 2025 (Year: 2021).

Weight Module Measuring Equipment, Hopper Weighing Module, www.web.archive.org/web/20210422161926/http://modul-ves.ru/catalog/bunkernye-vesy/vesovoy-modul-dlya-bunkera/, Apr. 22, 2021, translated via Google Translate, accessed Sep. 10, 2025 (Year:2025).

U.S. Appl. No. 17/833,682, filed Jun. 6, 2022 Advisory Action dated Mar. 24, 2026.

U.S. Appl. No. 17/873,834, filed Jul. 26, 2022 Advisory Action dated Jan. 30, 2026.

U.S. Appl. No. 17/873,834, filed Jul. 26, 2022 Non-Final Office Action dated Mar. 12, 2026.

U.S. Appl. No. 17/941,941, filed Sep. 9, 2022 Advisory Action dated Apr. 7, 2026.

U.S. Appl. No. 17/941,941, filed Sep. 9, 2022 Final Office Action dated Jan. 30, 2026.

U.S. Appl. No. 18/612,745, filed Mar. 21, 2024 Non-Final Office Action dated Apr. 1, 2026.

U.S. Appl. No. 18/682,075, filed Feb. 7, 2024 Advisory Action dated Mar. 6, 2026.

U.S. Appl. No. 18/682,082, filed Feb. 7, 2024 Non-Final Office Action dated Feb. 11, 2026.

U.S. Appl. No. 18/701,916, filed Apr. 16, 2024 Non-Final Office Action dated Mar. 23, 2026.

Wilson Npl Swir Imaging 101 https://~wilson.com/swir-imaging-101-what-can-it-do-for-you/ Jan. 2021 (Year: 2021).

* cited by examiner

URINE OUTPUT COLLECTION AND MONITORING SYSTEMS, DEVICES, AND METHODS

PRIORITY

This application claims the benefit of priority to U.S. Provisional Application No. 63/225,300, filed Jul. 23, 2021, which is incorporated by reference in its entirety into this application.

BACKGROUND

Presently, nearly all physiological parameters of a patient admitted to a critical care unit are sensed automatically by sophisticated commercial monitoring devices. This provides clinicians with invaluable information for interpreting the patient's state. In most cases, these devices can also supervise whether the values of the physiological parameters they sense remain within a pre-established range set by the clinician. This range represents the values considered as acceptable for each parameter. If a parameter does not fall within its acceptable range, audible warnings to alert the health care staff are generated. These devices discharge the healthcare staff of a considerable workload, since they need not continuously supervise whether the physiological parameters of every patient lie within the acceptable range. They also avoid human errors, which are common in any repetitive and monotonous task such as the supervision of physiological parameters.

It has been stated that the most relevant physiological parameter which is still measured and supervised manually by healthcare staff is urine output. Urine output is the best indicator of the state of the patient's kidneys. If the kidneys are producing an adequate amount of urine, it means that they are well perfused and oxygenated. Otherwise, it is a sign that the patient is suffering from some complication. Urine output is required for calculating the patient's water balance, which is essential in the treatment of burn patients. Finally, it is also used in multiple therapy protocols to check whether the patient reacts properly to treatment. When urine output is too low, the patient is said to have oliguria. If the patient does not produce urine at all, then he/she is said to have anuria. Sometimes, urine output can be too high; in these cases, the patient is said to have polyuria.

It is common to measure urine output by collecting urine in a graduated container. Periodically the nursing staff manually records the reading of the container of every patient, and operates a valve which releases the urine into a larger container. As such, the healthcare staff does not benefit from the advantages of having an automated determination and recording of urine output, or of the continuous and automatic supervision of its values. In critical care units, measurements of most every patient's urine output are often taken hourly, 24 times a day, 365 days a year. Furthermore, the monitoring of urine output for patients outside of the clinical setting is beneficial as well. As such urine collection devices that can be operated by the user/patient at home, for example, provide for urine output monitoring in the absence of a clinician. Transmitting the urine output data to the clinician provides for telemetric supervision of urine output values.

System and devices such as those described herein would decrease the workload associated with this collecting and monitoring urine output and, at the same time, permit supervision to take place on a more continuous basis resulting in better patient outcomes.

SUMMARY OF THE INVENTION

Briefly summarized, disclosed herein is a medical device for monitoring urine output from a patient, generally including a urine receiving device and a collection container coupled with the urine receiving device. The collection container includes a portion that change color in accordance with the collection of urine. In other words, the collection container displays a first color when a first volume of urine is disposed within the container and a different second color when a second volume of urine (different from the first volume) is disposed within the container. A tube may connect the container to the urine receiving device.

In some embodiments, the container includes a material disposed on an inside surface of a translucent container wall and a portion of the material displays the first color when the first volume of urine is disposed within the container, and the portion of the first material displays the second color when the second volume of urine is disposed within the container.

In some embodiments, the material is a hydrochromic ink, and the ink displays the first color when not wetted by the urine within the container, and ink displays the second color when wetted by the urine within the container.

In some embodiments, the container includes a flexible wall disposed within the container, where the flexible wall forms a first shape when the first volume of urine is disposed within the container, and the flexible wall forms a second shape when the second volume of urine is disposed within the container. In some embodiments, the flexible wall expands when wetted by the urine to transition from the first shape to the second shape.

In some embodiments, the flexible wall includes a hologram film, where the hologram film displays the first color when disposed in the first shape, and displays the second color when disposed in the second shape. A fluid force may act on the hologram film to transition the hologram film away from the first shape toward the second shape as the urine volume transitions away from the first volume toward the second volume.

In some embodiments, the container includes another material disposed on the inside surface of a translucent container wall, a portion of the other material displays the first color when wetted by the urine having a first pH, and displays the second color when wetted by urine having a second pH. The container may also an assay disposed on an inside surface of the container, where the assay configured for measuring a protein content of the urine.

In some embodiments, the receiving device is an external catheter, which may also be a female external catheter. The female external catheter may be secured to the patient via labia of the patient. The container may also be bag and the bag may be configured for attachment to a leg of the patient.

Also disclosed herein is another medical device for monitoring urine output from a patient, including (i) a urine receiving device, (ii) a collection container coupled with the urine receiving device, and (iii) a console coupled with the container. The console includes logic stored in memory that, when executed by one or more processors, causes performance of operations that include rendering information on a display pertaining a volume of collected urine within the container.

The operations may further include rendering a first color on the display when a first volume of urine is disposed within the container, and rendering a second different color on the display when a second volume of urine is disposed within the container, the second volume different from the first volume.

In some embodiments, the container includes a first flexible wall extending along an inside surface of a first container wall. A portion of the first flexible wall is separated away from the first container wall a first distance when the first volume of urine is disposed within the container, and the portion of the first flexible wall is separated away from the first container wall a second different distance when the second volume of urine is disposed within the container.

In some embodiments, the container includes a capacitive sensor coupled with the first container wall, where the capacitive sensor is configured to detect a capacitance of the space extending between the first container wall and the first flexible wall. The capacitive sensor detects a first capacitance when the first flexible wall is separated from the first container wall the first distance, and the capacitive sensor provides a first capacitance signal to the console in accordance with the first volume. The capacitive sensor also detects a second capacitance when the first flexible wall is separated from the first container wall the second distance, and the capacitive sensor provides a second capacitance signal to the console in accordance with the second volume.

In some embodiments, the container includes a second flexible wall extending along an inside surface of a second container wall opposite the first container wall. A portion of the second flexible wall is disposed away from the portion of the first flexible wall a first separation distance when the first volume of urine is disposed within the container, where the urine disposed between the first flexible wall and the second flexible wall. The portion of the second flexible wall is disposed away from the portion of the first flexible wall a second separation distance when the second volume of urine is disposed within the container, and the second separation distance is different from the first separation distance.

In such an embodiment, the capacitive sensor is configured to detect a fluid capacitance extending between the first container wall and the second container wall. The capacitive sensor detects a first fluid capacitance when the second flexible wall is separated from the first flexible wall the first separation distance, and the capacitive sensor provides a first capacitance signal to the console in accordance with the first volume. The capacitive sensor also detects a different second fluid capacitance when the second flexible wall is separated from the first flexible wall the second separation distance, and the capacitive sensor provides a second capacitance signal to the console in accordance with the second volume.

The container may include a salt sensor coupled with the console. The salt sensor is configured to provide a salt signal to the console in accordance with a salt content of the urine, and the operations further include rendering information on the display in accordance with the salt content of the urine.

The container may also include a protein sensor coupled with the console. The protein sensor is configured to provide a protein signal to the console in accordance with a protein content of the urine, and the operations further include rendering information on the display in accordance with the protein content of the urine.

The container may also include a pH sensor coupled with the console. The pH sensor is configured to provide a pH signal to the console in accordance with a pH of the urine, and the operations further include rendering information on the display in accordance with the pH of the urine.

The medical device may further include a support structure coupled with the receiving device, where the support structure is configured to facilitate hands-free use of the medical device. The support structure may include a seat and the support structure may be adjustable in height.

Also disclosed herein is a wearable medical device for assessing a bladder volume. The device includes a volume sensor configured to determine a volume of urine within the bladder of a patient, and an attachment mechanism coupled with the sensor. The attachment mechanism configured to attach the sensor to the patient adjacent the bladder of the patient. The device further includes a console coupled with the sensor, the console including logic stored in memory that, when executed by one or processors, causes performance of operations that include measuring a volume of urine within the bladder, and rendering on a display information pertaining to the measured volume. The device may include a skin color.

The attachment mechanism includes an adhesive configured to secure the device to a skin of the patient and the attachment mechanism may be configured to facilitate separation of the device from the skin and reattachment of the device to the skin. The attachment mechanism is configured to secure the volume sensor in direct contact with the skin. In some embodiments, the attachment mechanism comprises a panel coupled to and extending away from the volume sensor, and the adhesive is disposed on an underside of the panel.

The volume sensor may include an ultrasound transducer and the operations may further include ultrasonically obtaining a plurality dimensions of the bladder, and correlating the plurality dimensions with the volume of urine within the bladder.

The operations may further include wirelessly transmitting the information to an external device.

In some embodiments, the operations include ultrasonically determining a position of the bladder with respect to the position of the device on the patient, and providing a notification to the user when the device is correctly positioned.

The operations may also include comparing a bladder volume measurement with one or more bladder volume limits stored in memory, and as a result of the comparison, providing (i) a first notification when the urine volume measurement is within the one or more limits, and (ii) a second notification when the urine volume measurement exceeds any of the one or more limits. In some embodiments, providing the first notification includes illuminating a light emitting device of a first color, and providing the second notification includes illuminating a light emitting device of a different second color.

The console may include a battery power source, and the operations may include comparing a battery level with a low power limit stored in memory. As a result of the comparison, the operations may include illuminating a light emitting device in a blinking fashion when the battery level is below the low power limit.

Also disclosed herein is a medical system. The system a first device that includes the medical device for assessing a bladder volume summarized above and a non-transitory computer-readable storage medium (CRM) including executable instructions that when executed by one or more processors causes the one or more processors to perform operations, that include receiving bladder volume data from the first device, and rendering bladder volume information on a display. The CRM may be stored on a cellular phone.

The operations may further include comparing the bladder volume data with one or more volume limits of the CRM and as a result of the comparison, the operations may further include generating a user alert.

The operations may further include maintaining a historical record of the bladder volume data. The operations may also include transmitting the bladder volume data across a network to an external entity, where the external entity may be a healthcare provider.

In some embodiments, the system may further a second device that includes the medical device for monitoring urine output from a patient summarized above, and the operations may further include receiving collected urine volume data from the second device, and rendering collected urine volume information on a display. The operations further include maintaining a historical record of the collected urine volume data and transmitting the collected urine volume data across a network to the external entity.

The operations further include receiving urine chemical data from the second device and rendering urine chemical information on a display. The operations may further include maintaining a historical record of the urine chemical data and transmitting the urine chemical data across a network to the external entity.

The operations may further include comparing the urine chemical data with one or more urine chemical limits of the CRM, and as a result of the comparison, generating one or more user alerts.

Also disclosed herein is a method of monitoring a urine output of a patient, including (i) receiving a volume of urine from the patient via a receiving device, (ii) collecting the volume of urine within a container coupled to the receiving device, and (iii) automatically determining the volume of urine collected within the container.

The method may further include displaying a first color when a first volume of urine is collected within the container, and displaying a second color when a second volume of urine is collected within the container, where the second volume is different from the first volume, and the second color is different from the first color.

The method may further include automatically determining chemical parameters of the urine collected within the container, where the chemical parameters include one or more of a protein content, a salt content, and a pH level. The method may further include automatically transmitting one or more of the volume, protein content, salt content, or pH determinations to a healthcare provider.

In some embodiments, the method further includes automatically determining a volume of urine within a bladder of the patient via a wearable bladder volume assessment device attached to the patient, and the method may further include automatically transmitting the bladder volume determination to the healthcare provider.

These and other features of the concepts provided herein will become more apparent to those of skill in the art in view of the accompanying drawings and the following description, which describe particular embodiments of such concepts in greater detail.

BRIEF DESCRIPTION OF DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION

Figure 1A:
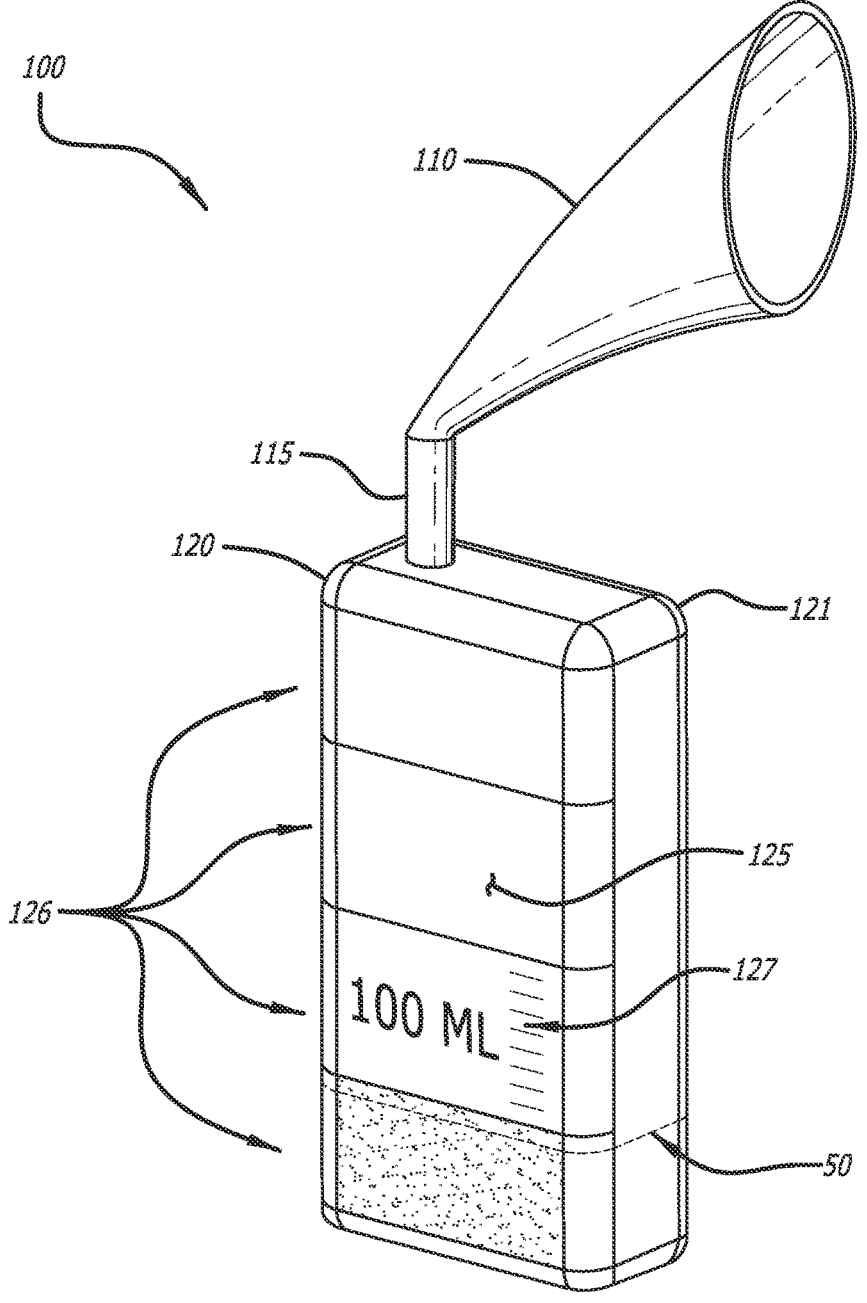
FIG. 1A illustrates a first embodiment of a urine collection device, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise. The words "including," "has," and "having," as used herein, including the claims, shall have the same meaning as the word "comprising." Furthermore, the terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, components, functions, steps or acts are in some way inherently mutually exclusive.

The phrases "connected to" and "coupled to" refer to any form of interaction between two or more entities, including mechanical, electrical, magnetic, electromagnetic, fluid, signal, communicative (including wireless), and thermal interaction. Two components may be connected or coupled to each other even though they are not in direct contact with each other. For example, two components may be coupled to each other through an intermediate component.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

The directional terms "proximal" and "distal" are used herein to refer to opposite locations on a medical device. The proximal end of the device is defined as the end of the device closest to the end-user when the device is in use by the end-user. The distal end is the end opposite the proximal end, along the longitudinal direction of the device, or the end furthest from the end-user.

Unless defined otherwise, all technical and scientific terms used herein have the same meaning as commonly understood by those of ordinary skill in the art.

FIG. 1A illustrates a first embodiment of a urine collection device, in accordance with some embodiments disclosed herein. The urine collection device 100 generally include a fluid receiving component 110 fluidly coupled with a collection container 120 via a tube 115. In use, urine 50 is expelled by a patient into the fluid receiving component 110 where it flows through the tube 115 into the collection container 120. The collection container is configured to indicate parameters of the collected urine 50 to a user. The user may be the patient, a clinician, or any other support person. The parameters may include physical parameters and/or chemical parameters. The collection container 120 may be sized to receive a full amount of urine 50 as may be expelled by an adult patient.

The collection device 100 may be configured for manual grasping and positioning by the user while urine 50 is expelled into the receiving component 110. In some embodiments, the tube 115 may be relatively short (e.g., 1-4 inches in length) and sufficiently stiff so that the user may grasp the collection container 120 to position the receiving component 110. In other embodiments, the tube 115 may be relatively long (e.g., 2-5 feet in length) and sufficiently flexible so that the user may grasp and position the receiving component 110 while the collection container 120 positioned separate from the user, such as on the floor, for example.

The collection container 120 may be sufficiently rigid to retain its shape during use. In some embodiments, the collection container 120 may be rectangular in shape. A bottom side of the collection container 120 may be configured for stable placement on a horizontal surface in an upright orientation. The tube 115 may be coupled with the collection container 120 toward an upper end of the collection container 120 to prevent urine 50 from exiting the collection container 120 through the tube 115 when the collection container 120 is disposed in the upright orientation. In some embodiments, the receiving component 110 and/or the tube 115 may be selectively coupled with and decoupled from the collection container 120.

In the illustrated embodiment, one or more visible parameters of the collection container 120 may change in response to the presence of urine 50 within the collection container 120. For example, the collection container 120 may define a vertically oriented wall 125. Segments 126 of the wall 125 may visibly change in accordance with a volume of urine 50 present within the collection container 120. The segments 126 of the wall 125 may be arranged vertically along the wall 125. In use, each segment 126 may change visibly as the level of urine 50 exceeds the vertical position of the segment 126. For example, each segment 126 may change from a first color to a second color (e.g., from red to green, light to dark, etc.) when the level of urine 50 exceeds the vertical position of the segment 126. As such, the clinician may quickly and easily ascertain the volume of urine 50 expelled from the patient into the collection device 100.

Each segment 126 may represent the volume of urine 50 present in the collection container 120 in decreet increments, such as 10 ml, 20 ml and so forth. In other embodiments, the segments 126 may be small enough to continuously indicate the volume of urine 50 over a defined range, such as 10 ml to 1000 ml, for example. In some embodiments, the collection container 120 may include a transparent portion to allow the clinician to inspect the collected urine 50. In some embodiments, the collection container 120 may include indicia 127. The indicia 127 may include, graduation lines, volume information, or any other markings associated with operation of the collection device 100.

Figures 1B, 1C:
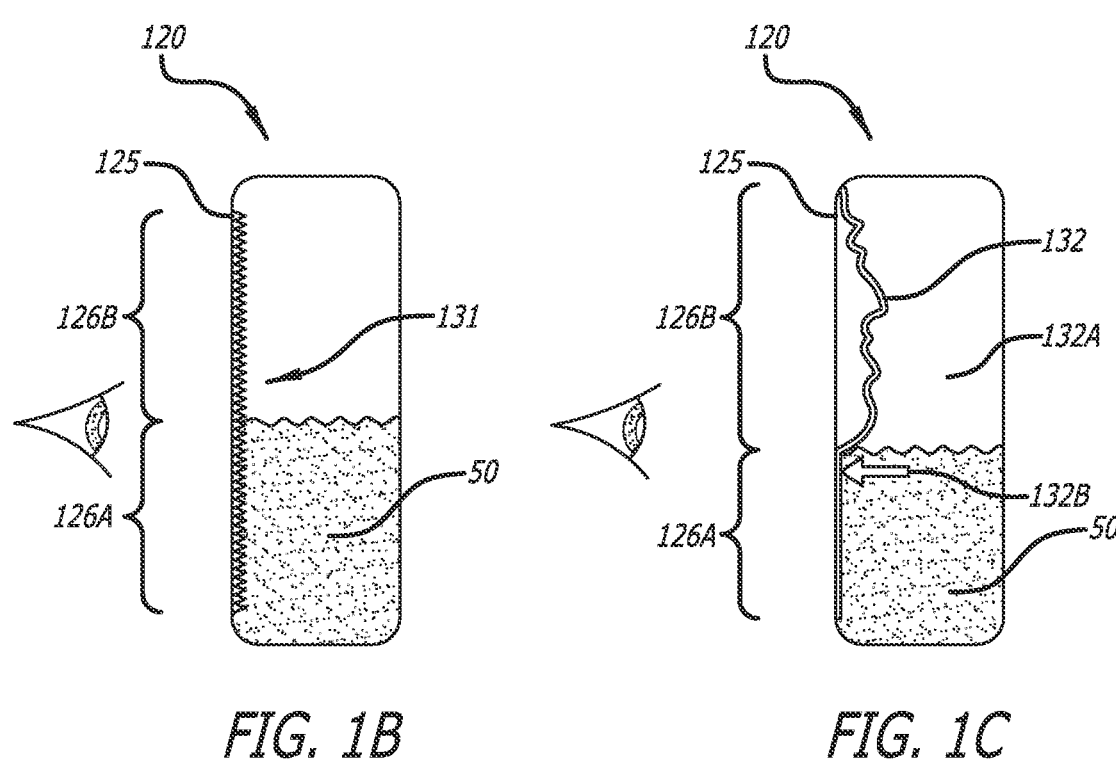
FIGS. 1B-1D are side view illustrations of a collection container of the urine collection device FIG. 1A showing various mechanisms that facilitate a visible color change of the collection container according to volume of urine 50 within the collection container, in accordance with some embodiments.
Figures 1D, 1E, 1F:
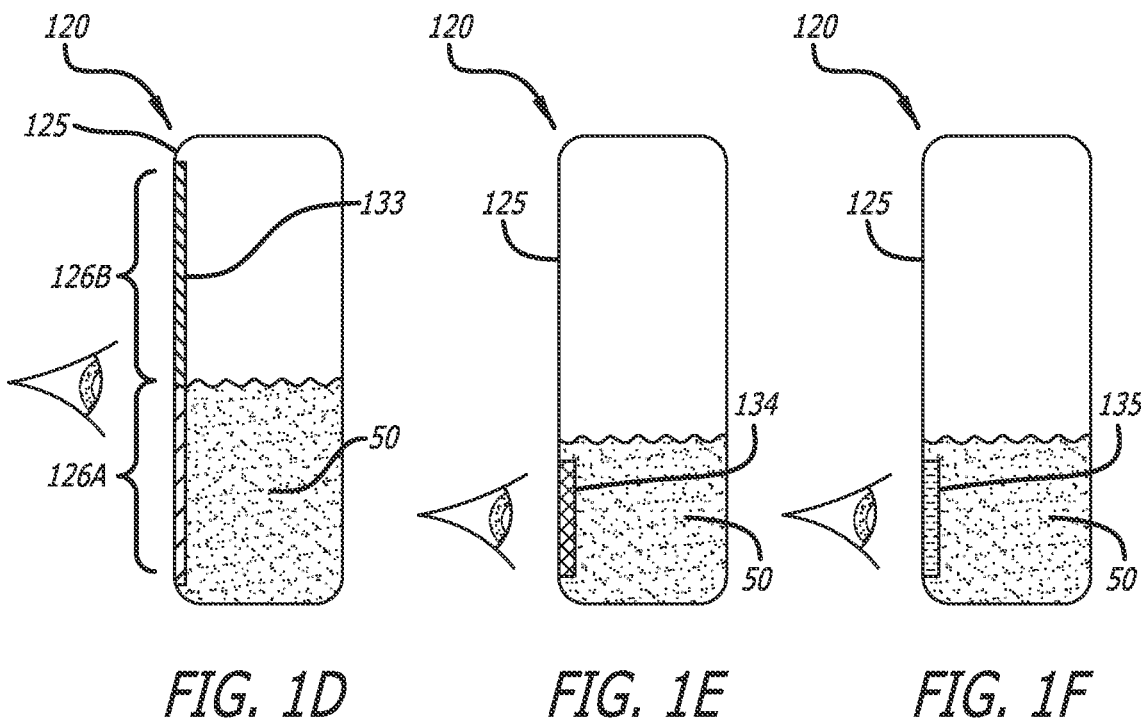
FIG. 1E illustrates a mechanism of the collection container of FIG. 1A that facilitates a visible color change of the container according to a pH of a urine within the collection container, in accordance with some embodiments.
FIG. 1F illustrates a mechanism of the collection container of FIG. 1A that facilitates a visible color change of the container according to protein content of a urine within the collection container, in accordance with some embodiments.

FIGS. 1B-1D illustrate various structures of the collection container 120 that may facilitate the visible change according to the level of urine 50 within the collection container 120. FIG. 1B shows a cross-sectional side view of the container 120 including the vertical wall 125. In one exemplary embodiment, the vertical wall 125 may be transparent/translucent having a hydrochromic ink 131 disposed on an inner surface of the wall 125. The hydrochromic ink is configured to change color when the ink is exposed to urine 50. Hence, in use, the hydrochromic ink 131 causes the segments 126A to display one color in response to contact of the hydrochromic ink 131 with the urine 50 when viewed through the wall 125. Conversely, the segments 126B display a different color due to a lack of contact with the urine 50.

In another exemplary embodiment, the collection container 120, or a portion thereof, is formed of a flexible holographic film that is configured to refract light of different colors when viewed from different angles. In such an embodiment, the viewing angle of the holographic film may change when a fluid force of the urine 50 acts on the holographic film causing a change in color. FIG. 1C shows a cross-sectional side view of the container 120 including the vertical wall 125 which is transparent/translucent. A holographic film 132 forms a portion of a bladder 132A within the collection container 120. In use, the urine 50 exerts a fluid force 132B on the holographic film 132 to displace the holographic film 132 in contact with the vertical wall 125 causing flat shape of the holographic film 132. The flat shape of the holographic film 132 causes the segments 126A to display a first color pattern of when viewed through the vertical wall 125. Conversely, a non-flat shape of the holographic film 132 above the level of urine 50 causes the segments 126B to display a second color pattern when viewed through the vertical wall 125.

In still another exemplary embodiment, the collection container 120 includes a material that has a first color when dry and a second color when wetted by the urine 50. FIG. 1D shows a cross-sectional side view of the container 120 including the vertical wall 125 which is transparent/translucent. A material 133 (e.g., a paper) is attached to an inside surface of the vertical wall 125. In use, the urine 50 wets the material 133 causing the segments 126A to display a first color when viewed through the vertical wall 125. Conversely, the dry portion of the material 133 above the level of urine 50 causes the segments 126B to display a second color when viewed through the vertical wall 125.

The collection container 120 may also be configured to provide one or more visual notifications of one or more chemical parameters of the urine 50 which may be indicative of a patient health, specifically kidney health. Chemical parameters may include, but are not limited or restricted to, pH, salt content, and/or protein content. FIG. 1E shows a cross-sectional side view of the container 120 including the vertical wall 125 which is transparent/translucent. In an exemplary embodiment, a litmus paper 134, configured to display a color in accordance with a pH level of the urine 50, is disposed on an inner surface of the wall 125 adjacent a bottom side of the collection container 120. In use, the urine 50 wets the litmus paper 134 causing the litmus paper 134 to display a color according to a pH of the urine 50 which may be viewed through the vertical wall 125. As such, the clinician may ascertain pH of the urine 50 by viewing the collection container 120. In alternative embodiments, the litmus paper 134 may be located on any inside surface of the collection container 120.

FIG. 1F shows a cross-sectional side view of the container 120 including the vertical wall 125 which is transparent/translucent. In an exemplary embodiment, a protein test strip 135, configured to display a color in accordance with a protein content within the urine 50, is disposed on an inner surface of the wall 125 adjacent a bottom side of the collection container 120. In use, the urine 50 wets the protein test strip 135 causing the protein test strip 135 to display a color according to a protein content within the urine 50 which may be viewed through the vertical wall 125. As such, the clinician may ascertain the protein content within the urine 50 by viewing the collection container 120. In alternative embodiments, the protein test strip 135 may be located on any inside surface of the collection container 120. In yet another embodiment, one or more inner surfaces of the container 120 may be covered or coated with certain materials common to protein test strips and/or urine test strips. These reagents may test the urine for blood, bilirubin, urobilinogen, nitrite, leucocytes (white blood cells), protein, ketones, glucose, pH, and specific gravity (relative density).

Figure 2A:
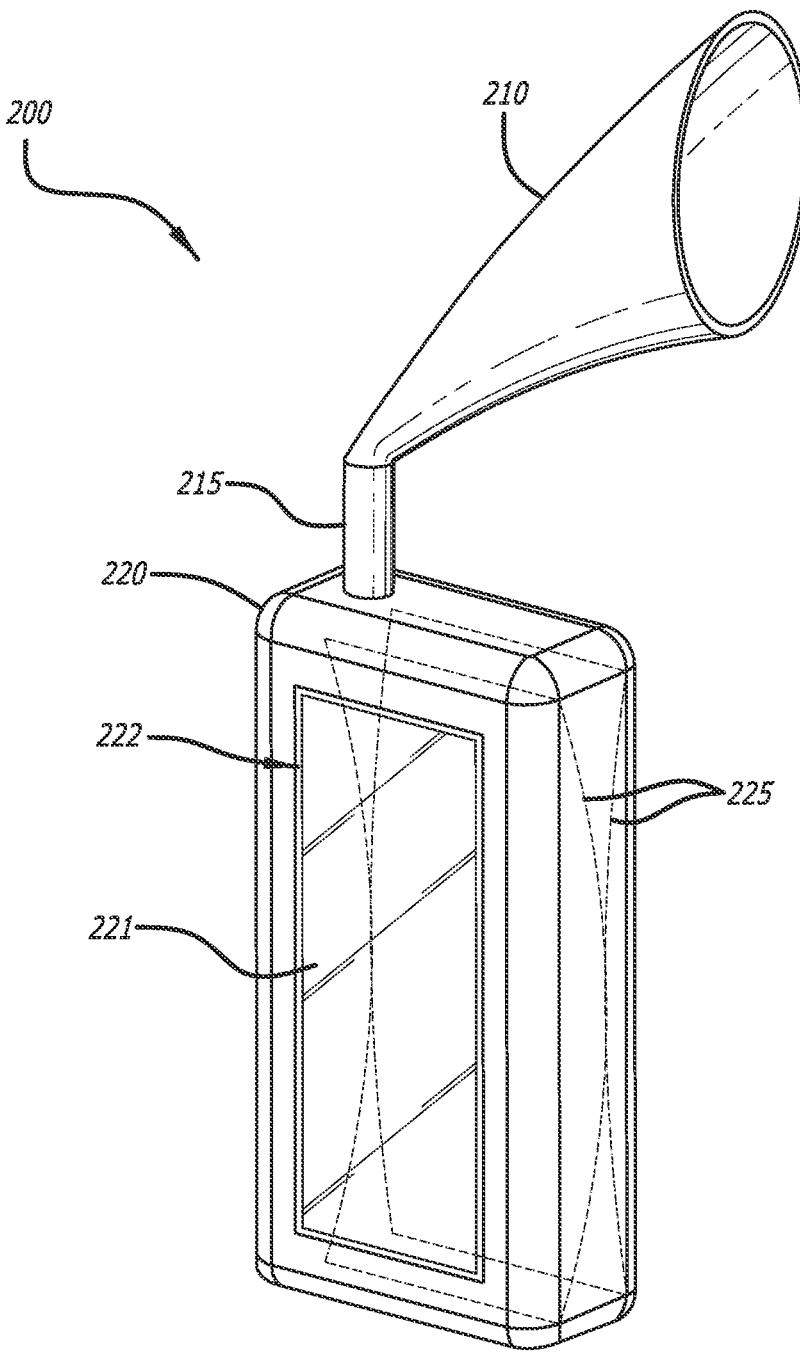
FIG. 2A illustrates a second embodiment of a urine collection device, in accordance with some embodiments.

FIG. 2A illustrates a second embodiment of a urine collection device 200 that can, in certain respects, resemble components of the collection device 100 described in connection with FIGS. 1A-1E. It will be appreciated that all the illustrated embodiments may have analogous features. Accordingly, like features are designated with like reference numerals. Relevant disclosure set forth above regarding similarly identified features thus may not be repeated hereafter. Moreover, specific features of the collection device 100 and related components shown in FIGS. 1A-1E may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the collection device 200 of FIGS. 2A-2C. Any suitable combination of the features, and variations of the same, described with respect to the collection device 100 and components illustrated in FIGS. 1A-1E can be employed with the collection device 200 and components of FIGS. 2A-2C, and vice versa. This pattern of disclosure applies equally to further embodiments depicted in subsequent figures and described hereafter. Additionally, all embodiments disclosed herein are combinable and/or interchangeable unless stated otherwise or such combination or interchange would be contrary to the stated operability of either embodiment.

The urine collection device 200 generally includes a fluid receiving component 210 fluidly coupled with a collection container 220 via a tube 215. In use, urine 50 is expelled by a patient into the fluid receiving component 210 where it flows through the tube 215 into the collection container 220. The collection container 220 is configured to provide indications to a clinician or user regarding parameters of the collected urine 50. The parameters may include physical parameters and/or chemical parameters.

The urine collection device 200 is also generally configured to transmit urine related data/information to a network device, such as a computer or a cell phone, for example via a console 222, discussed below. In some embodiments, the urine collection device 200 may transmit urine related data/information to a healthcare provider which may be included in an electronic medical record (EMR) for the patient.

The urine collection device 200 is configured to define an electronic signal in accordance with a volume of urine 50 collected within the collection container 220. In the illustrated embodiment, the collection container 220 includes a film 225. The film 225 is configured to change shape in response to the presence of urine 50 within the collection container 220. The film 225 may change shape in response to exposure to the urine 50. In other words, the film 225 may define a first shape when dry and a second shape when wetted by the urine 50. In some embodiments, the film 225 may continuously change from the first shape to the second shape as the volume of urine 50 increases within the collection container 220. In some embodiments, the urine 50 may contact a single side of the film 225 and in other embodiments, the urine 50 may contact both sides of the film 225. In some embodiments, a property of the film 225 may change due to exposure to the urine 50. For example, the film 225 may become more flexible when exposed to the urine 50. In other embodiments, internal stresses within the film 225 may be relieved when exposed to urine 50. In still other embodiments, portions of the film 225 may absorb the urine 50 and swell in response to the absorption causing the film 225 to change shape. The urine 50 may exert a force on the film 225 causing the film 225 to change shape.

Figure 2C:
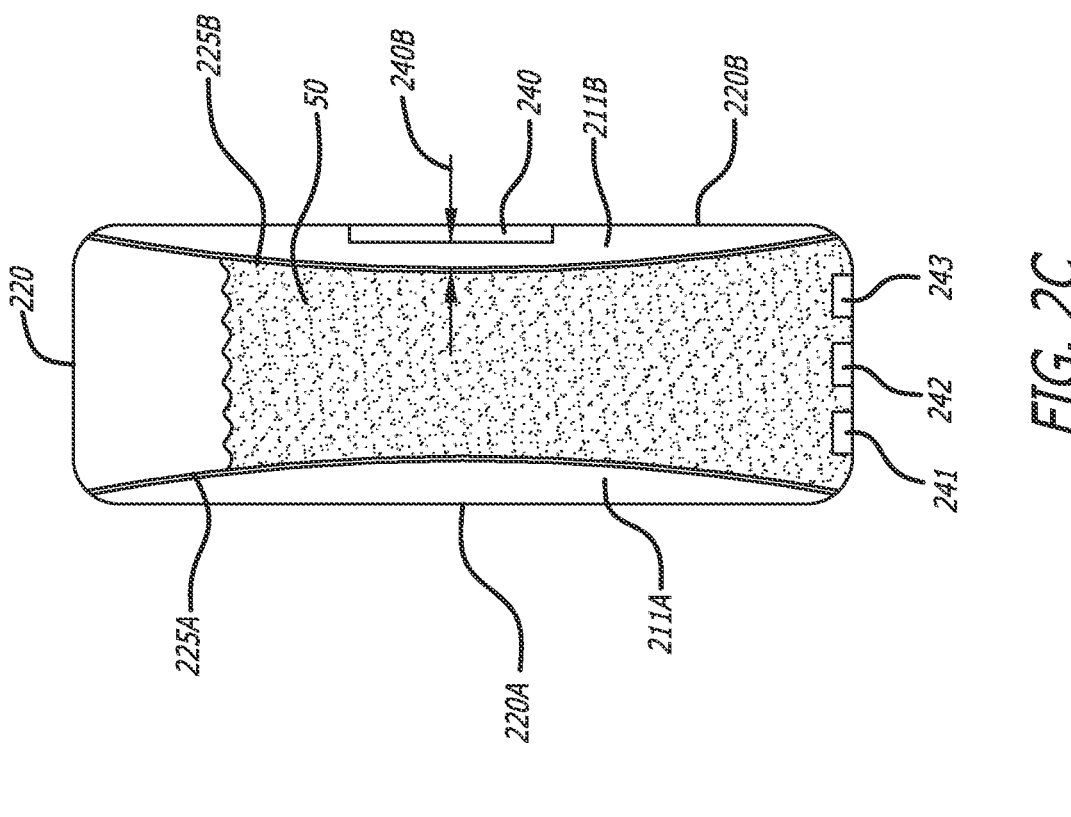
FIGS. 2B-2C are side view illustrations of the container of the urine collection device of FIG. 2A showing a volume sensor in a first state and a second state of operation, in accordance with some embodiments.
Figure 2B:
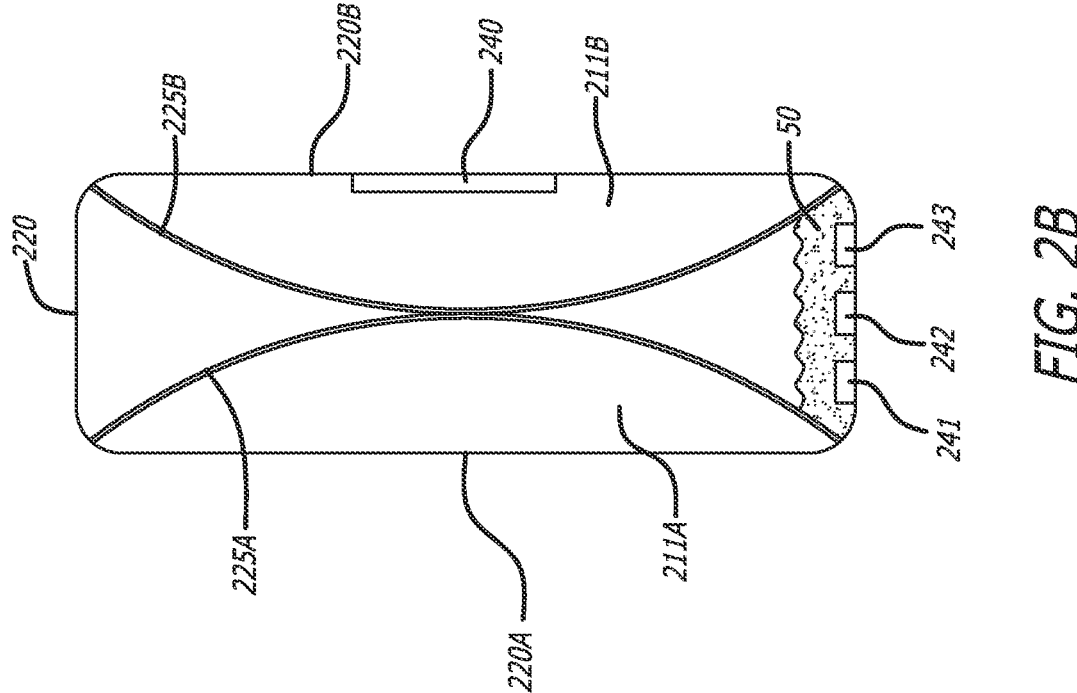

FIGS. 2B and 2C illustrate volume measurement mechanism as may be employed by the collection container 220. FIG. 2B is a cross-section side view of the collection container 220 having minimal urine 50 therein. A first film 225A extends inward from a first side 220A of the collection container 220 defining a gap 211A, and a second film 225B extends inward from an opposite second side 220B defining a gap 211B. In the illustrated embodiment, the urine 50 is contained between the first film 225A and the second film 225B so that the gaps 211A, 211B contain air.

FIG. 2C is a cross-section side view of the collection container 220 having a greater volume of urine 50 therein than depicted in FIG. 2B. In FIG. 2C, the first film 225A is displaced toward the first side 220A in relation to the position of the film 225A in FIG. 2B. Similarly, the second film 225B is displaced toward the second side 220B in relation to the position of the film 225B in FIG. 2B. As such, the gaps 211A, 211B are smaller in FIG. 2C than in FIG. 2B.

A volume sensor 240 is coupled to the second side 220B. In alternative embodiments, the volume sensor 240 may be coupled with the first side 220A or volume sensors 240 may be coupled with both the first side 220A and the second side 220B. The volume sensor 240 is configured to generate an electrical signal in accordance with a distance 240B across the gap 211B. As such, the volume of urine 50 within the collection container 220 may be correlated with the electrical signal.

The volume sensor 240 may be a capacitive sensor configured to relate an electrostatic capacitance with the distance 240B according to the equation 1 below, where C is the capacitance, S is the area of the sensor, $\varepsilon$ is the dielectric of air, and D is the gap distance (i.e., the distance 240B). In use, the capacitance is converted into an electrical signal that is directly related to the distance 240B.

$$C = \frac{\varepsilon S}{D} \qquad \text{Equation 1}$$

In some implementations, the capacitance may be measured across a thickness of the collection container 220 (i.e., between the sides 220A, 220B). In such an implementation, the dielectric & may be related to the portion of the thickness that is filled with urine 50 which may be defined by the distance between the films 225A, 225B.

In alternative embodiments, the volume sensor 240 may be pressure sensor (not shown) disposed at a bottom of the collection container 220 or embedded into the film 225. The volume sensor 240 may also be a proximity sensor (not shown) disposed at the top or bottom of the collection container 220, where the proximity sensor is configured to determine height of the urine 50 within the collection container 220.

With further reference to FIGS. 2B and 2C, the collection container 220 may include sensors for determining/measuring one or more chemical conditions of the collected urine 50. The sensors may include a salt sensor 241 configured to measure a conductivity of the collected urine 50. The salt sensor may measure conductivity which may be related to osmolality which in turn may be related to salt content. As conductivity measurement is affected by temperature, the salt sensor 241 may include a temperature sensor (not shown).

The collection container 220 may include a protein sensor 242 operably coupled with the console 222. The protein sensor 242 may be disposed at a bottom portion of the collection container 222 so that a minimal volume of collected urine 50 may contact the protein sensor 242. The protein sensor 242 is configured to provide an electrical signal to the console 222 in accordance with a concentration of protein within the collected urine 50.

The collection container 220 may include a pH sensor 243 operably coupled with the console 222. The pH sensor 243 may be disposed at a bottom portion of the collection container 222 so that a minimal volume of collected urine 50 may contact the pH sensor 243. The pH sensor 243 is configured to provide an electrical signal to the console 222 in accordance with a pH of the collected urine 50.

Figure 3:
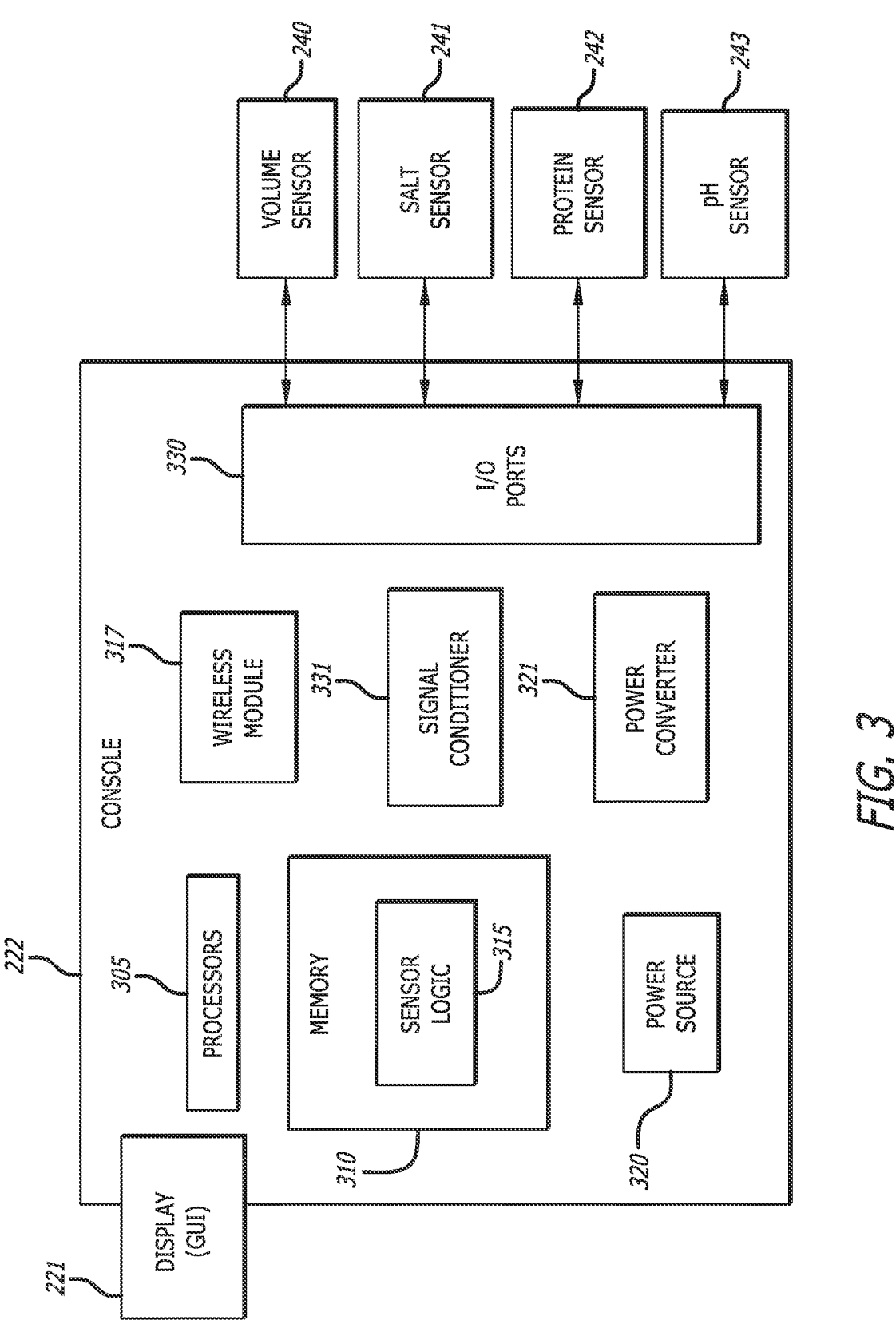
FIG. 3 is a block diagram of a console of the urine collection device of FIG. 2A, in accordance with some embodiments.

FIG. 3 illustrates a block diagram of the console 222 of FIG. 2A, in accordance with some embodiments. The console 222 includes a one or more processors 305 and memory 310 including a non-transitory, computer-readable storage medium. Stored in the memory 310 is sensor logic 315. A power source 320 provides electrical power to the console 222 including the console components. The volume sensor 240, salt sensor 241, protein sensor 242, and pH sensor 243 are each coupled with the console 222 via the I/O ports 330. The electrical power passes through a power converter 321 to facilitate the operation of each of the sensors 240-243, and electrical signals from the sensors 240-243 pass through the signal conditioner 331 for processing by the sensor logic 315. The console 112 may include or be coupled with the display 221. A wireless module 317 facilitates communication and data sharing with external devices and/or networks. The sensor logic 315 is configured to control each of the sensors 240-243 and process data received from each of the sensors 240-243.

The power source 320 may be an internal battery or an external power source such as a facility power source, and the power converter 321 converts the electrical power from the power source 320 into forms of electrical power compatible with each of the sensors 240-243. The power converter 320 may be controllable via the sensor control logic 315 when executed by the processors 305 to enable/disable each of the sensors 240-243.

The display 221 is coupled to the console 222 via a wired or wireless connection. In some embodiments, the display 222 includes an operator interface such as a graphical user interface (GUI), for example. In some embodiments, the display 221 may be disposed within or otherwise incorporated into the housing 121 of the collection container 120.

The display 221 may provide visual notifications in various forms. The display 221 may render indica on a screen, such as alpha or numerical characters, for example. By way of further example, the display 221 may provide visual notification in the form of colored objects, such as lights, portions of a screen, and the like. In some embodiments, the display 221 may include light emitting devices, such as an array of LEDs (not shown), including LEDs of different colors, disposed along an outside surface of the collection container 220.

In some embodiments, the sensor logic 315 may cause LEDs of different colors to be illuminated in accordance with data received from the volume sensor 240 pertaining to a collected volume of urine 50. For example, LEDs of a first color may be illuminated indicating a collection of urine 50 below a defined volume and LEDs of a second color may be illuminated indicating a collection of urine 50 above the defined volume. In some embodiments, LEDs may be positioned along a height of the collection container 120, so that an illuminated LED may indicate a level of urine 50 within the collection container 120. It is understood that other forms of visual notification, in addition to the examples described above, may be contemplated by one of ordinary skill. As such, any and all other forms of indicating to a user a volumetric status of collected urine 50 are disclosed herein. Similarly, the display 221 may also provide notification pertaining to data received from the salt sensor 241, the protein sensor 242, and/or pH sensor 243.

In some embodiments, the sensor logic 315 may provide notification of data from one or more of the sensors 214-243 exceeding one or more defined limits stored in memory 310. For example, the logic 315 may cause the display to flash or blink when the collected volume exceeds a predefined "full" limit. In some embodiments, the console 222 may include an audio device (not shown) and the logic 315 may cause an alarm to be sounded when data from one or more of the sensors 214-243 exceeds one or more defined limits stored in memory 310.

In some embodiments, the sensor logic 315 may causes data received from the sensors 240-243 to recorded for analysis at a later time. The logic 315 may also transmit processed data from the sensors 240-243 to an external device or network. In some embodiments, the display 221 may be an external device, such as a computer, a tablet, a cell phone, or a network component.

The sensor logic 315 may enable and/or disable the any of the sensors 240-243. For example, in some embodiments, one or more of the sensors 241-243 may require a defined volume of collected urine 50 for operation. As such, the logic 315 may enable a sensor only if the collected volume of urine 50 exceeds the defined volume requirement for operation. By way of another example, the logic 315 may enable a given sensor or otherwise cause data to be collected from the given sensor, according to defined time intervals or sub-volumes of collected urine 50, or after a may enable and/or disable the any of the sensors 240-243. In some embodiments, the logic 315 may also define an operating mode or operating range of a sensor.

The sensor logic 315 may also monitor a power level of power source (e.g., battery). The sensor logic 315 may compare the power level with a low power limit stored in memory 310 and as a result of the comparison, provide a notification to the user when the power level is below the low power limit. In some embodiments, the notification may include illuminating a light emitting device in a blinking fashion.

Figure 4:
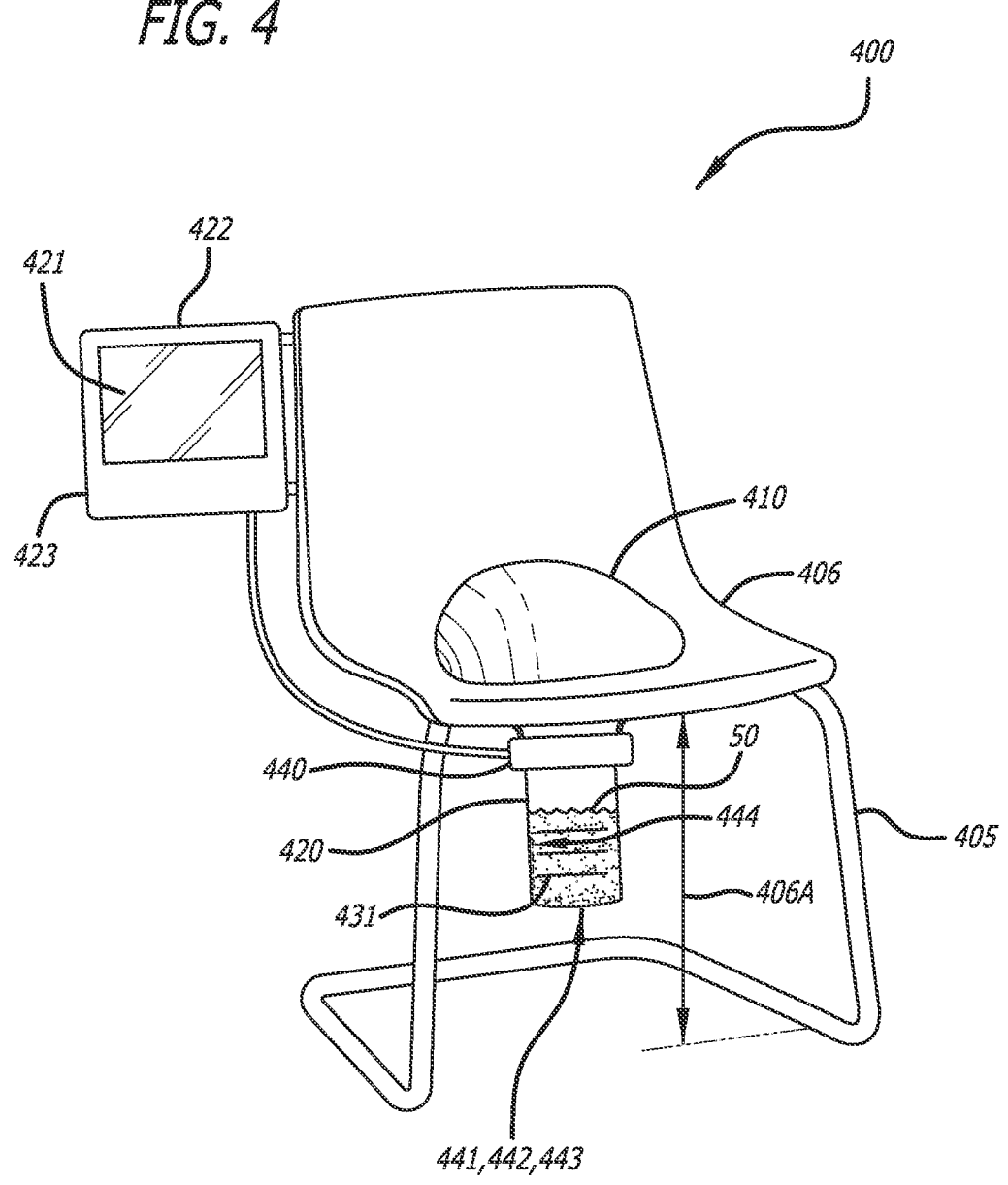
FIG. 4 illustrates a third embodiment of a urine collection device, in accordance with some embodiments.

FIG. 4 illustrates a third embodiment of a urine collection device, in accordance with some embodiments disclosed herein. The urine collection device 400 is configured as a "smart" urine hat/commode. The urine collection device 400 generally includes a collection container 420 including a receiving component 410 combined therewith. In some embodiments, the collection container 420 may be separable/removable from the receiving component 410. In use, urine 50 is expelled by a patient into the fluid receiving component 410 where it flows into the collection container 420. The collection container 420 is configured to provide indications to a clinician or user regarding parameters of the collected urine 50. The parameters may include physical parameters and/or chemical parameters.

The urine collection device 400 may include a support structure 405 configured to receive the collection container 420. The support structure 405 facilitates automatic collection of the urine 50 in a hands-free manner. Some embodiments of the urine collection device 400 may be configured for female patients and other embodiments of the urine collection device 400 may be configured for male patients. In other words, the shape and/or orientation of some embodiments of the receiving component 410 may be configured for receiving urine 50 from female patients, and the shape and/or orientation of other embodiments of the receiving component 410 may be configured for receiving urine 50 from male patients. Additionally, embodiments of the support structure 405 may include a seat 406 for female patients and other embodiments of the support structure 405 may omit the seat 406 for male patients. In some embodiments, a height 406A of the support structure 405 may be adjustable to accommodate patients of different sizes. In some embodiments, the collection container 410 may be configured to interface with a facility structure, such as a toilet or urinal, for example, in which embodiments, the support structure 405 may be omitted.

The collection container 420 includes a volume sensor 440. The volume sensor 440 may be configured to measure a weight of the collected urine 50. For example, in some embodiments, the volume sensor 440 may include one or more strain gauges disposed along a side wall of the collection container 420. A measured strain of the strain gauges may be correlated with the weight of the collected urine 50 which may then be converted to volume via a specific gravity of the urine 50. Other alternative weight measurement devices could be incorporated into the collection container 420 and are therefore included within this disclosure. The collection container 420 may also include indicia 431, such as volumetric graduation lines, for example.

In some embodiments, the collection container 420 may include assay materials/components 444 disposed on an inside surface of the collection container 420. The assay components 444 may facilitate chemical analysis of the urine 50, such as protein measurement/analysis, for example.

Similar to the urine collection device 200 described above, the urine collection device 400 may also include a console 422 including a display 421 disposed within a housing 423. As such the urine collection device 400 is configured to transmit urine volumetric data/information to a network device, such as a computer or a cell phone, for example. In some embodiments, the urine collection device 400 may transmit urine related data/information to a healthcare provider which may be included in an electronic medical record (EMR) for the patient. In some embodiments, the housing 423 may be attached to the support structure 405.

In some embodiments, the collection container 420 may also include a salt sensor 441, a protein sensor 442, and/or a pH sensor 443. As such the urine collection device 400 may also be configured to measure and transmit chemical parameter data/information of the collected urine 50.

Figure 5:
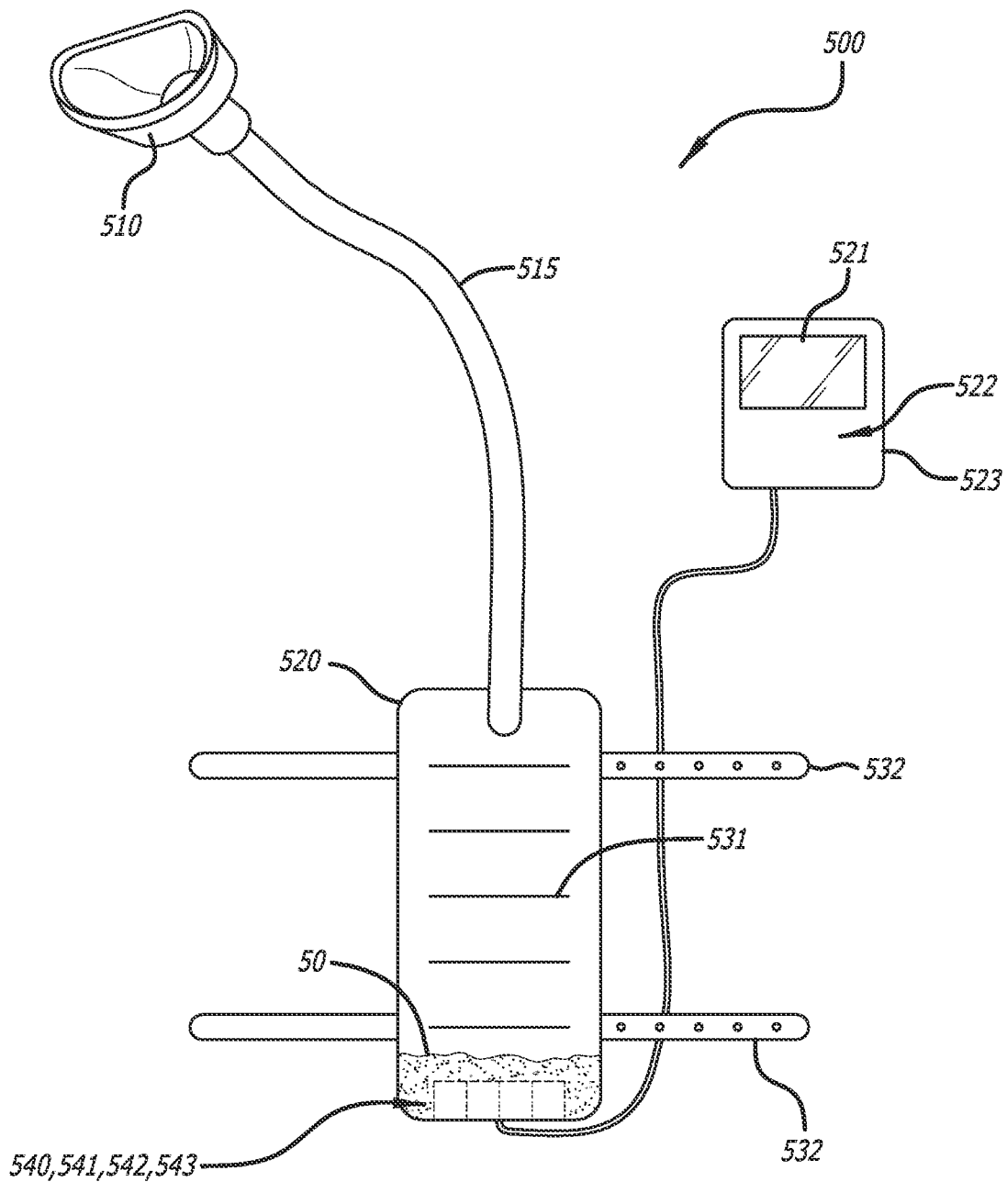
FIG. 5 illustrates a fourth embodiment of a urine collection device, in accordance with some embodiments.

FIG. 5 illustrates a fourth embodiment of a urine collection device, in accordance with some embodiments disclosed herein. The urine collection device 500 generally includes a collection container 520 coupled with a receiving component 510 via a tube 515. The collection container 520 may be configured as a "smart" bag that is attachable to a patient's leg via an attachment mechanism 532 (e.g., straps). In some embodiments, the collection container 520 may be separable/removable from the receiving component 510. In use, urine 50 is expelled by a patient into the fluid receiving component 510 where it flows into the collection container 520 via the tube 515. The collection container 520 is configured to provide indications to a clinician or user regarding parameters of the collected urine 50. The parameters may include physical parameters and/or chemical parameters.

In some embodiments of the receiving component 510 may be a female external catheter which may be held in place via female anatomy (e.g., labia). The female external catheter may reduce the risk of catheter-associated urinary tract infections (CAUTI). The female external may be configured to remain in place as the patient walks. In other embodiments, the receiving component 510 may be a male external catheter.

The collection container 520 includes a volume sensor 540. In one exemplary embodiment, the volume sensor 540 may be configured to measure a weight of the collected urine 50 which is converted to volume via the specific gravity of the urine 50. In another embodiment, the volume sensor 540 may include a force sensor (e.g., a film type force sensor) configured to provide an electrical signal in accordance with an applied force. The force sensor may intergrade into a wall of the container 520 or coupled to an inside surface of the wall. The force sensor may be positioned so that fluid force applied to the sensor is related to fluid volume within the container 520. The collection container 520 may also include indicia 531, such as volumetric graduation lines, for example.

Similar to the urine collection device 200 described above, the urine collection device 500 may also include a console 522 including a display 521 disposed within a housing 523. As such the urine collection device 500 is configured to transmit urine volumetric data/information to a network device, such as a computer or a cell phone, for example. In some embodiments, the urine collection device 500 may transmit urine related data/information to a healthcare provider which may be included in an electronic medical record (EMR) for the patient. The housing 523 may be configured for attachment to the patient (e.g., clipped to a belt, placed in a pocket, etc.).

In some embodiments, the collection container 520 may also include a salt sensor 541, protein sensor 542, and/or a pH sensor 543. As such the urine collection device 500 may also be configured to measure and transmit chemical parameter data/information of the collected urine 50.

Figure 6:
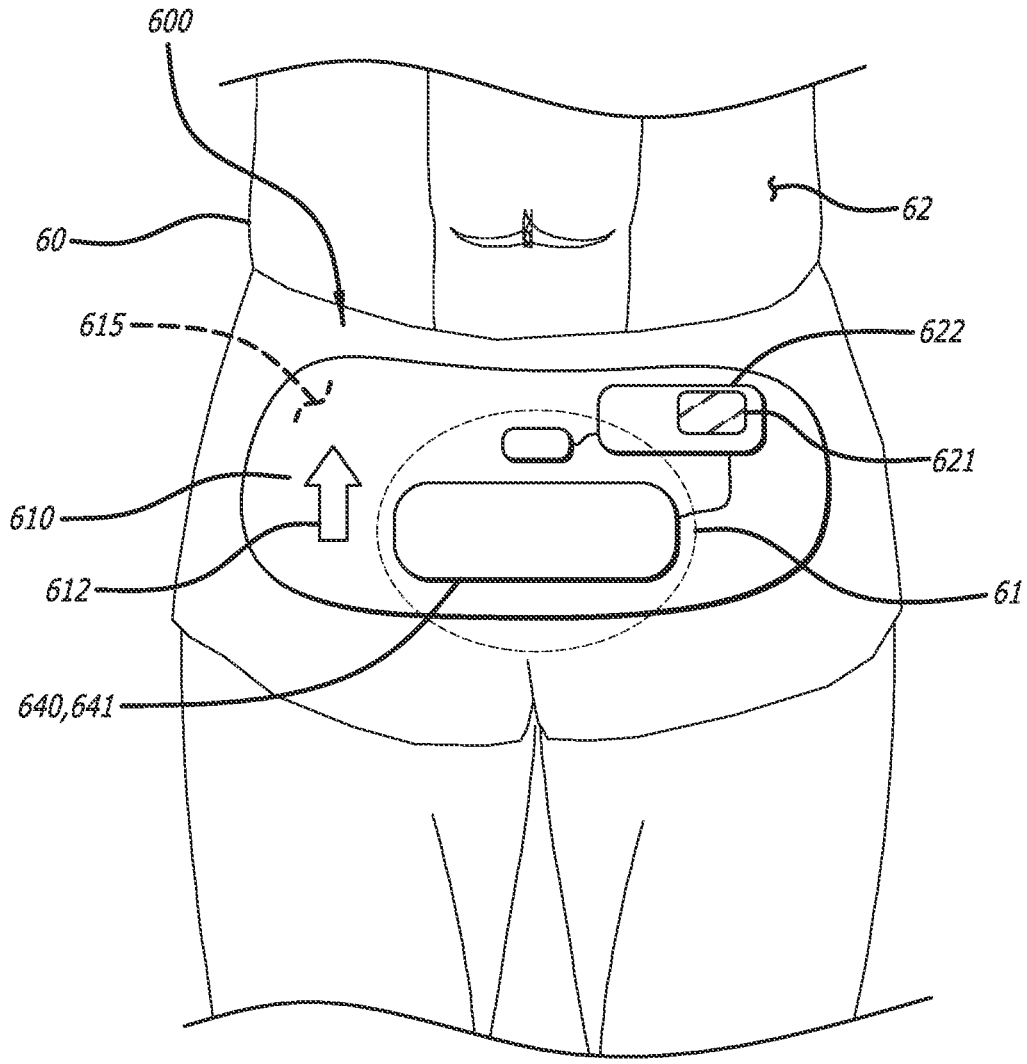
FIG. 6 illustrates an embodiment of a bladder volume assessment device, in accordance with some embodiments.

FIG. 6 illustrates a bladder volume assessment device, in accordance with some embodiments. The bladder volume assessment device 600 is a wearable device configured to measure a volume of urine 50 within a bladder 61 of a patient 60. The device 600 generally includes bladder volume sensor 640 which may include an ultrasound transducer 641. The ultrasound transducer 641 is attached to a panel 610. An adhesive 615 disposed on an underside of the device 600 secures the device 600 to the patient 60. The adhesive 615 may be disposed on the underside of the panel 610 and/or the ultrasound transducer 641. In use, the ultrasound transducer 641 is placed in contact with the skin 62 of the patient 60 adjacent the bladder 61. The adhesive 615 secures the bladder volume device 600 to the skin 62 of the patient 60. In some embodiments, an ultrasound gel (not shown) may be placed between the ultrasound transducer 641 and the skin 62 to enhance the transmission of ultrasound waves between the ultrasound transducer 641 and patient 60. The ultrasound transducer 641 is operably coupled with a console 622 which may include an operator interface 621. In some embodiments, the operator interface 621 may be omitted.

The panel 610 may be formed of a flexible or semi-flexible sheet material. The panel 610 may encircle and extend radially outward from the ultrasound transducer 641.

The panel 610 may include indica 612 such as an alignment arrow or markings to aid in the placement of the device 600 on the patient 60.

The device 600 may be configured for separation from and reattachment to the patient 60. In some embodiments, the adhesive 615 may be configured for separation of the from the skin 62 via alcohol.

The device 600 may also include a bladder location sensor 650 coupled with the console 622. The bladder location sensor 650 may be configured to identify a location of the bladder 61 with respect to a location of the bladder volume sensor 640. The bladder location sensor 650 may include an ultrasound transducer 651 configured to provide an electrical signal to the console 622 in accordance with a location of the bladder 61 relative to a location of the bladder volume sensor 640. In some embodiments, the bladder location sensor 650 may employ the ultrasound transducer 641 of the bladder volume sensor 640 in which embodiment, the ultrasound transducer 651 may be omitted.

Figure 7:
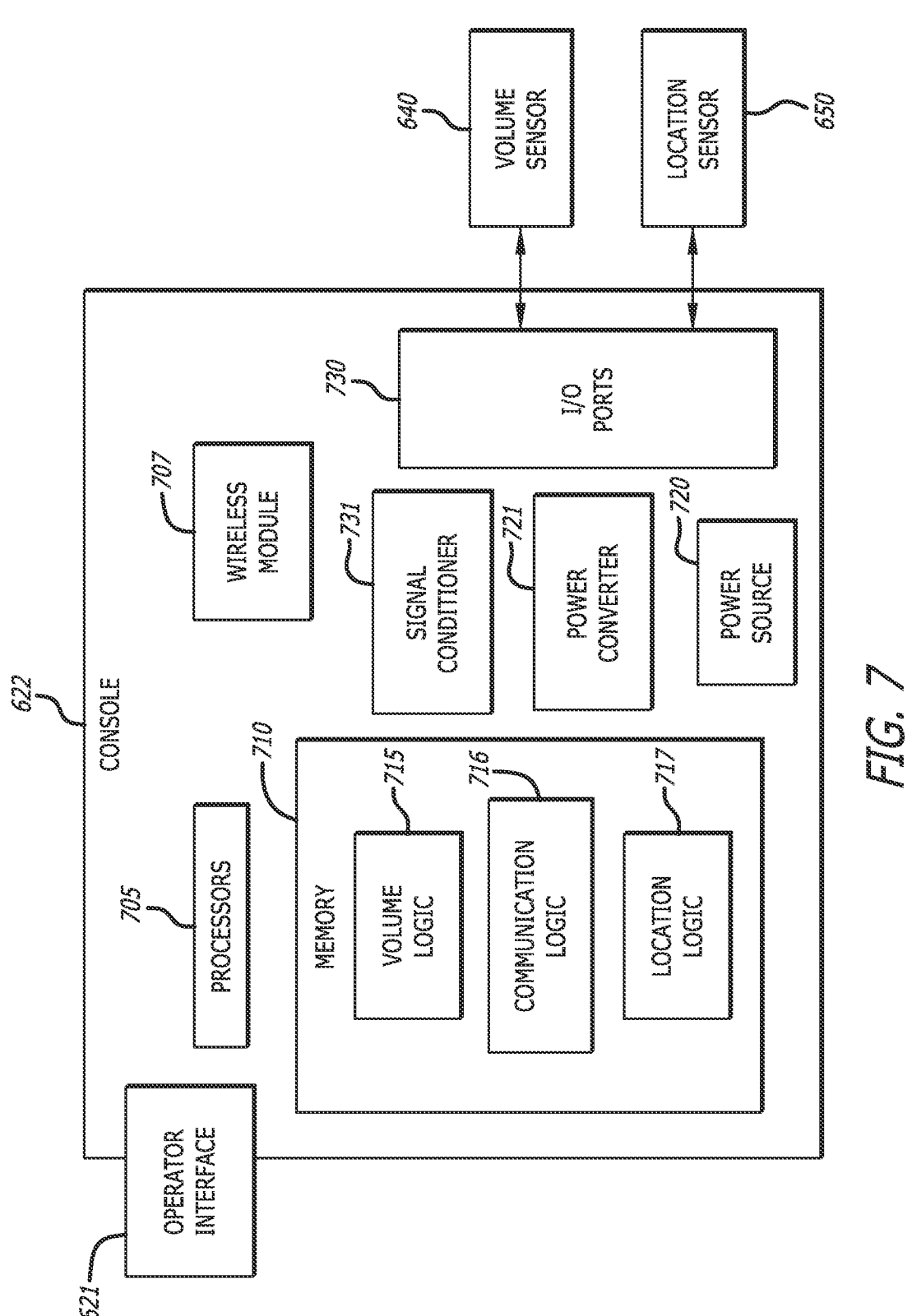
FIG. 7 is a block diagram of a console of the bladder volume assessment device of FIG. 6, in accordance with some embodiments.

FIG. 7 illustrates a block diagram of the console 622 of FIG. 6, in accordance with some embodiments. The console 622 includes a one or more processors 705 and memory 710 including a non-transitory, computer-readable storage medium. Stored in the memory 710 are volume logic 715, communication logic 716, and location logic 717. A power source 720 provides electrical power to the console 622 including the console components. The volume sensor 640 and the location sensor 650 are coupled with the console 622 via the I/O ports 730. The electrical power passes through a power converter 721 which in turn powers the ultrasound transducer 641 of the volume sensor 640 and the ultrasound transducer 651 of the location sensor 640. Electrical signals from the ultrasound transducer 641 and the ultrasound transducer 651 pass through the signal conditioner 731 for processing by the volume logic 715 and location logic, respectively. A wireless module 717 facilitates communication and data sharing with external devices and/or networks.

The console 622 may include or be coupled with the user interface 621. The user interface may facilitate operation of the bladder volume device 600 by the patient 60 or another user. Although not required, the user interface 621 may include a graphical user interface display (GUI) for the rendering of information on a display and/or provide for input by the user. In some embodiments, the user interface 621 may include an audio device for providing audible alerts to the patient 60. In some embodiments, the user interface 621 may include light emitting devices, such as light emitting diodes (LEDs) including colored LEDs, for example.

The volume logic 715 is configured to operate the ultrasound transducer 641 and process data received from the ultrasound transducer 641. In some embodiments, the volume logic 715 may locate a volume of urine 50 within the bladder 61. The volume logic 715 may then obtain two or more distances extending between opposite inside surfaces of the bladder 61. The logic may then perform a volume calculation using the obtained distances to define the volume measurement of urine 50 within the bladder 61. In some embodiments, the volume logic 715 may obtain bladder volume measurements at defined intervals. In some embodiments, the volume logic 715 may obtain maximum and/or minimum bladder volume measurements over defined time periods. In further embodiments, the volume logic 715 may define rates of bladder volume change over defined time periods. In some embodiments, the volume logic 715 may compare bladder volume measurements with one or more bladder volume limits stored in memory 710, and as a result of the comparison provide an alert to the patient 60.

Examples of the alert may be, but are not limited or restricted to, (i) a sound, (ii) a visual indication such as a color change of the bladder volume device 600, a change of state of a light (e.g., off to on, or vice versa), or text or graphical indication displayed on the user interface 621 of the bladder volume device 600 in some embodiments, or (iii) vibration directly from the bladder volume device 600.

The location logic 717 may be configured to determine if the ultrasound transducer 641 is correctly placed for operation of the volume sensor 640. In some embodiments, the location logic 717 may determine a position of the bladder 61 in relation to the position of the ultrasound transducer 641. As a result of the relative position determination, the location logic 717 may provide a notification to the user. In some embodiments, the notification may be the illumination of a light emitting device having a color (e.g., green) when the ultrasound transducer 641 is correctly located in relation to the bladder 61.

The power source 720 may be an internal battery which may be rechargeable. The power converter 721 converts the electrical power from the power source 720 into a forms of electrical power compatible with the ultrasound transducer 641. The power converter 720 may be controllable via the volume logic 715 when executed by the processors 705 to enable/disable the ultrasound transducer 641. The wireless module 707 may facilitates communication between bladder volume device 600 and external devices as defined by the communication logic 716.

Figure 8A:
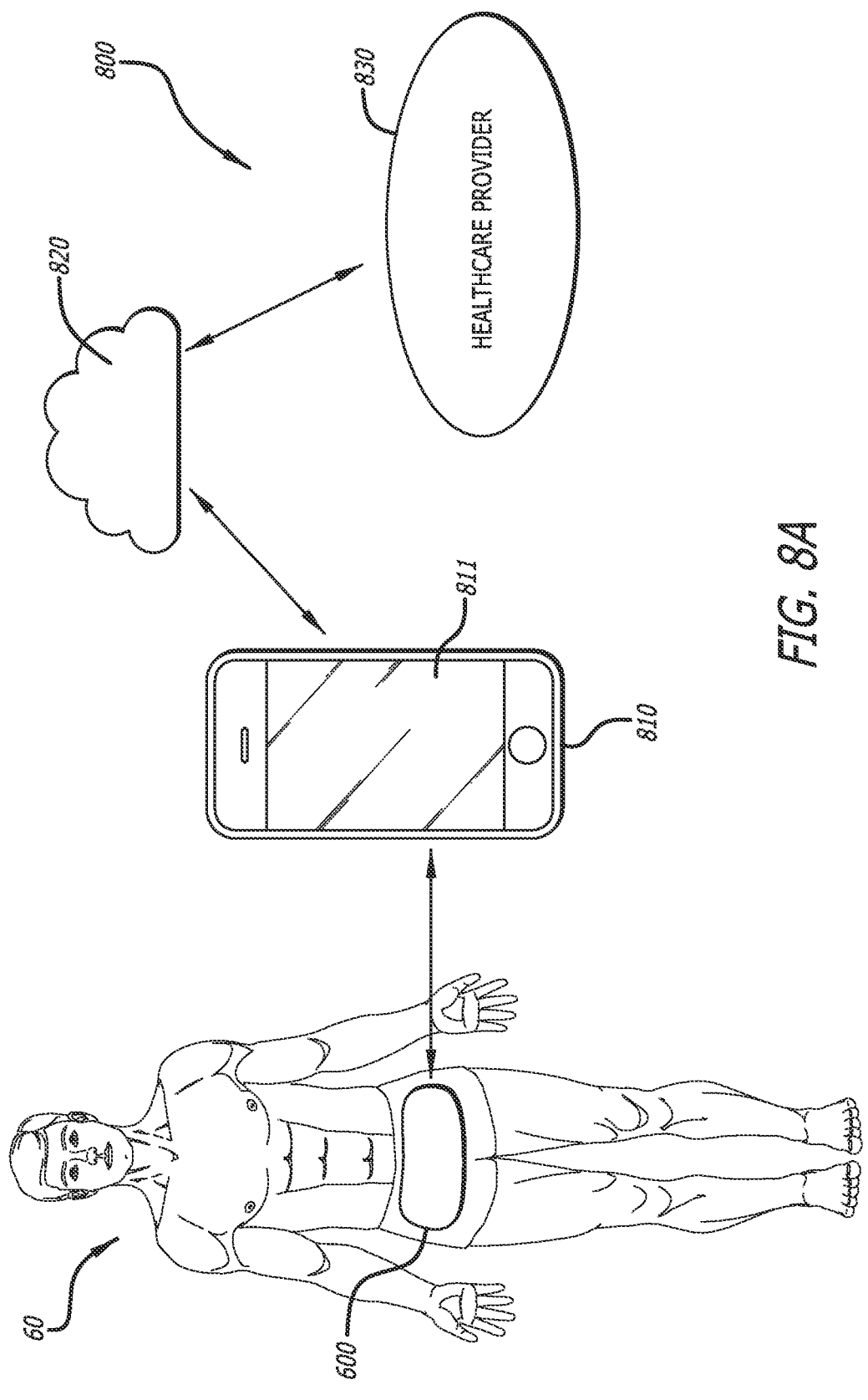
FIG. 8A illustrates a first embodiment of a medical system that includes the bladder volume assessment device of FIG. 6, in accordance with some embodiments.

FIG. 8A illustrates a first exemplary embodiment of a bladder volume system 800 including an architecture as illustrated. The bladder volume system 800 may include the bladder volume device 600, a user device 810 including logic 811 operating thereon, a network 820, and an external entity 830. The network 820 represents the communication pathways between the user device 810 and the external entity 830. In one embodiment, the network 820 is the Internet. The network 820 can also utilize dedicated or private communication links (e.g., WAN, MAN, or LAN) that are not necessarily part of the Internet. The network 820 may use standard communications technologies and/or protocols. In some embodiments, the logic 811 may be in the form of a software application that is loaded on the user device 810 and executable by hardware processing circuitry. In other embodiments, the logic 811 need not be loaded on the user device 810 but may instead execute within a cloud computing environment (which may also be represented by the reference numeral 820) such that data obtained or otherwise detected by bladder volume device 600 are communicated to the logic 811 for processing. Thus, any logic 811 represented as being part of the user device 810 may include an application programming interface (API) that is configured to transmit and receive data communication messages to and from the logic 811 operating in the cloud computing environment.

The user device 810 can be any device that incorporates logic (as well as hardware circuitry and non-transitory, computer-readable memory in instances in which logic refers to software). In some instances, the user device 810 executes an operating system, for example, a Microsoft Windows-compatible operating system (OS), Apple OS X or iOS, a Linux distribution, or Google's Android OS. In some embodiments, the user device 810 may use a web browser, such as Microsoft Internet Explorer, Mozilla Firefox, Google Chrome, Apple Safari and/or Opera, as an interface to interact with the logic 811.

The user device 810 is communicatively coupled to the bladder volume device 600 via a wireless protocol, e.g., Bluetooth, radio frequency, infrared, microwave, Zigbee, or any other suitable wireless protocol. In some embodiments, the user device 810 may be coupled to the bladder volume device 600 via a wired connection. The user device 810 sends operating commands to the bladder volume device 600 and receives bladder volume information or data from the bladder volume device 600.

The external entity 830 may be a person, an institution, or a cloud computing environment (e.g., cloud computing resources accessible via a network such as the internet). In some embodiments, the external entity 830 may be a healthcare provider for the patient 60. As such, it may be advantageous for the healthcare provider 830 to access bladder volume information of the user device 810 and thereby remotely monitor the bladder volume condition of the patient 60. In some embodiments, the system 800 may be configured to alert the healthcare provider of an extreme bladder volume condition or trend. In embodiments in which the external entity 830 is a cloud computing environment, the user device 810 may include a communication interface, such as a wireless transceiver, that is configured to transmit and receive data communication messages, which may include data obtained or otherwise detected by the bladder volume device 600 as discussed herein.

In some embodiments, the system 800 may include access to an electronic medical record (EMR) of the patient 60. In such embodiments, the EMR may automatically record bladder volume information for review by the healthcare provider 830 at a future consultation with the patient 60, for example.

Those of skill in the art will appreciate that the system 800 may contain other architectural modules that are not described herein. In addition, conventional elements, such as firewalls, authentication systems, payment processing systems, network management tools, load balancers, and so forth are not shown as they are not material to the invention. The system 800 may be implemented using a single user device 810 or a network of computers, including cloud-based computer implementations.

Figure 8B:
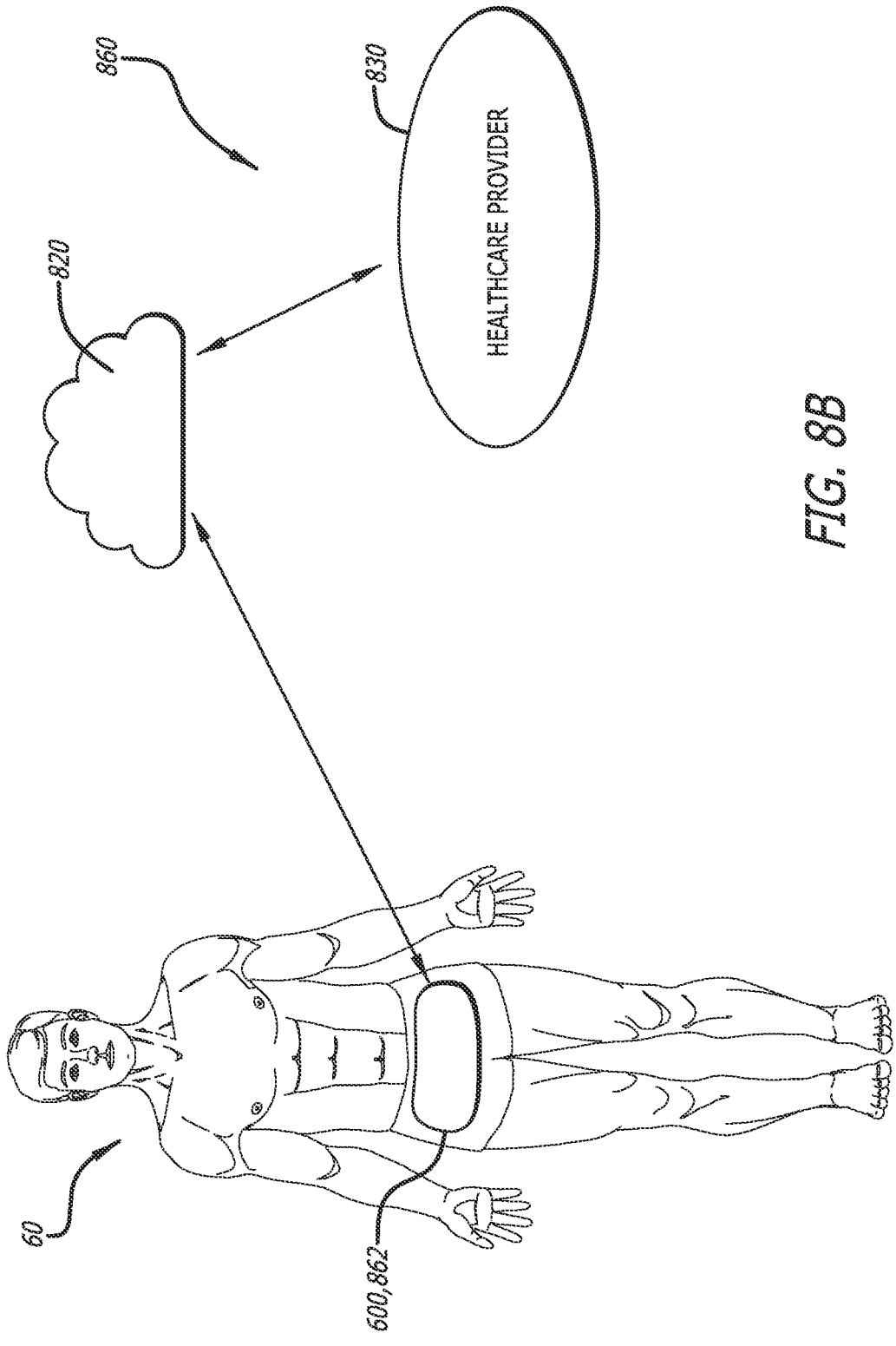
FIG. 8B illustrates a second embodiment of a medical system that includes the bladder volume assessment device of FIG. 6, in accordance with some embodiments.

FIG. 8B illustrates second exemplary embodiment of a bladder volume system 860 including an architecture as illustrated. The bladder volume system 860 may include the bladder volume device 600 including logic 862 operating thereon. In some instances, the bladder volume system 860 may include the network 820 and the external entity 830 as discussed above; however, such are not required.

In some embodiments, the logic 862 may be in the form of a software application that is loaded on the bladder volume device 600 and executable by hardware processing circuitry similarly included therein. In other embodiments, the logic 862, or a portion thereof, need not be loaded on the bladder volume device 600 but may instead execute within a cloud computing environment (which may also be represented by the reference numeral 820) such that bladder volume data obtained by the bladder volume device 600 are communicated to the logic 862 for processing. Thus, any logic 862 represented as being part of the bladder volume device 600 may include an application programming interface (API) that is configured to transmit and receive data communication messages to and from the logic 862 operating in the cloud computing environment. As a result, the system 860 of FIG. 8B may be utilized for processing any bladder volume data obtained by the bladder volume device 600 without any need for coupling with a user device. Thus, the bladder volume device 600 may obtain bladder volume data via the ultrasound transducer 641 therein, process the urine data with the logic 862 and hardware circuitry, and provide a notification to the healthcare provider 830 as described above.

Figure 9A:
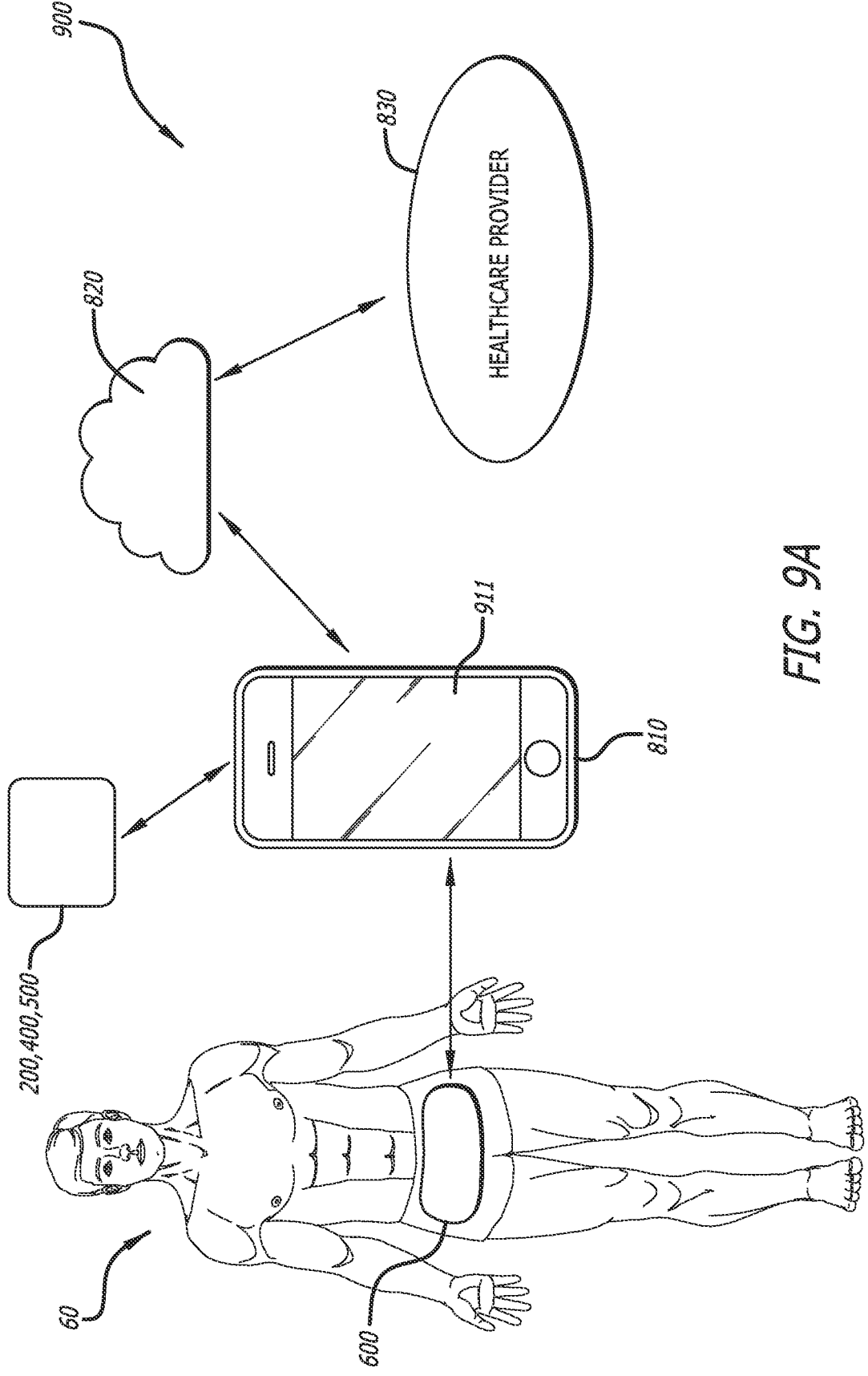
FIG. 9A illustrates a first embodiment of a medical system that includes the bladder volume assessment device of FIG. 6 and any of the urine collection devices of FIG. 2A, 4, or 5, in accordance with some embodiments.

FIG. 9A illustrates a first exemplary embodiment of a urine monitoring system 900 including an architecture as illustrated. The urine monitoring system 900 may include the bladder volume device 600, the user device 810 including logic 911 operating thereon, the network 820, the external entity 830, and one or more of the urine collection devices 200, 400, or 500, described above. The logic 911 may be in the form of a software application that is loaded on the user device 810 and executable by hardware processing circuitry. In other embodiments, the logic 911 need not be loaded on the user device 810 but may instead execute within a cloud computing environment (which may also be represented by the reference numeral 820) such that data obtained by bladder volume device 600 and the one or more of the urine collection devices 200, 400, or 500 are communicated to the logic 911 for processing. Thus, any logic 911 represented as being part of the user device 810 may include an application programming interface (API) that is configured to transmit and receive data communication messages to and from the logic 911 operating in the cloud computing environment.

The user device 810 is communicatively coupled to the bladder volume device 600 and the one or more of the urine collection devices 200, 400, or 500 via a wireless protocol, e.g., Bluetooth, radio frequency, infrared, microwave, Zigbee, or any other suitable wireless protocol. In some embodiments, the user device 810 may be coupled to the bladder volume device 600 or the one or more of the urine collection devices 200, 400, or 500 via a wired connection. The user device 810 sends operating commands to the bladder volume device 600 and the one or more of the urine collection devices 200, 400, or 500 and receives bladder volume information or data from the bladder volume device 600 and collected urine volume information or data from the one or more of the urine collection devices 200, 400, or 500. The user device 810 may also receive information or data from the one or more of the urine collection devices 200, 400, or 500 pertaining the chemical properties of the urine 50 described above in connection with the one or more of the urine collection devices 200, 400, or 500.

As the external entity 830 may be a healthcare provider for the patient 60, it may be advantageous for the healthcare provider 830 to access urine related information of the user device 810 and thereby remotely monitor the urine conditions of the patient 60. In some embodiments, the system 900 may be configured to alert the healthcare provider 830 of an extreme urine condition or trend.

In some embodiments, the system 900 may include access to the electronic medical record (EMR) of the patient 60. In such embodiments, the EMR may automatically record bladder volume, collected urine volume, and urine related information for review by the healthcare provider 830 at a future consultation with the patient 60, for example.

Figure 9B:
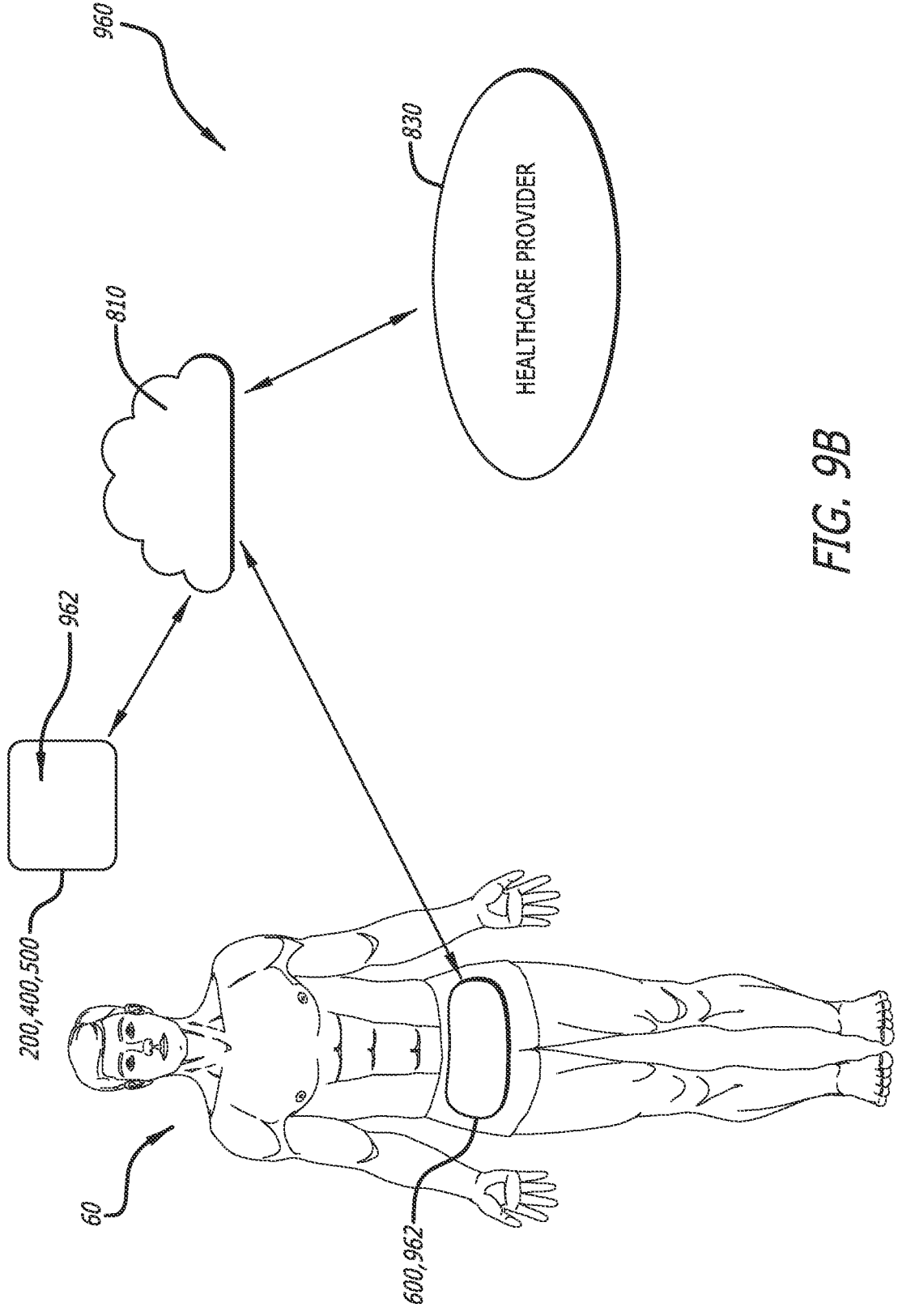
FIG. 9B illustrates a second embodiment of a medical system that includes the bladder volume assessment device of FIG. 6 and any of the urine collection devices of FIG. 2A, 4, or 5, in accordance with some embodiments.

FIG. 9B illustrates second exemplary embodiment of a urine monitoring system 960 including an architecture as illustrated. The urine monitoring system 960 may include the bladder volume device 600 and the one or more of the urine collection devices 200, 400, or 500 including logic 962 operating thereon. In some instances, the urine monitoring system 960 may include the network 820 and the external entity 830 as discussed above; however, such are not required.

In some embodiments, the logic 962 may be in the form of a software application that is loaded on the bladder volume device 600 and the one or more of the urine collection devices 200, 400, or 500 so as to be executable by hardware processing circuitry similarly included therein. In other embodiments, the logic 962, or a portion thereof, need not be loaded on the bladder volume device 600 and the one or more of the urine collection devices 200, 400, or 500 but may instead execute within a cloud computing environment (which may also be represented by the reference numeral 820) such that urine related data obtained by the bladder volume device 600 and the one or more of the urine collection devices 200, 400, or 500 are communicated to the logic 962 for processing. Thus, any logic 962 represented as being part of the bladder volume device 600 and the one or more of the urine collection devices 200, 400, or 500 may include an application programming interface (API) that is configured to transmit and receive data communication messages to and from the logic 962 operating in the cloud computing environment. As a result, the urine monitoring system 960 of FIG. 9B may be utilized for processing any urine related data obtained by the bladder volume device 600 and the one or more of the urine collection devices 200, 400, or 500 without any need for coupling with a user device. Thus, the bladder volume device 600 and the one or more of the urine collection devices 200, 400, or 500 may obtain urine data, process the urine data with the logic 962 and hardware circuitry, and provide urine related information to the healthcare provider 830 as described above.

A method of monitoring a urine output of a patient may include the following steps or process. The method may include receiving a volume of urine from the patient via the receiving device, and collecting a volume of urine within the container. The method may include automatically determining the volume of urine collected within the container via the volume sensor of the container. The method may include displaying a first color when a first volume of urine is collected within the container and displaying a second color when a second volume of urine is collected within the container. The method may further include (i) automatically determining a protein content of the urine within the container, (ii) automatically determining a salt content of the urine within the container, and/or automatically determining a pH of the urine within the container. Thereafter, the method may include automatically transmitting one or more of the volume, protein content, salt content, or pH determinations to a healthcare provider. The method may further include automatically determining a volume of urine within a bladder of the patient via a wearable bladder volume assessment device attached to the patient and automatically transmitting the bladder volume determination to a healthcare provider.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

What is claimed is:

1. A medical device for monitoring urine output from a patient, comprising:
   a urine receiving device;
   a collection container coupled with the urine receiving device, the collection container comprising:
      a first flexible wall having a urine contact surface and an outward facing surface; and
      a rigid first container wall having an inward facing surface extending along the outward facing surface; and
   a console coupled with the collection container, the console including logic stored in memory that, when executed by one or more processors, causes performance of operations including rendering information on a display pertaining to a volume of collected urine within the collection container.

2. The medical device of claim 1, wherein:
   the collection container comprises a pH sensor coupled with the console,
   the pH sensor is configured to provide a pH signal to the console in accordance with a pH of the collected urine, and
   the operations include rendering information on the display in accordance with the pH of the collected urine.

3. The medical device of claim 1, wherein:
   the collection container comprises a urine volume sensor coupled with the console,
   the urine volume sensor is configured to provide a volume signal to the console in accordance with the volume of the collected urine within the collection container, and
   the operations include rendering information on the display in accordance with the collected urine within the collection container.

4. The medical device of claim 3, wherein:
   the urine volume sensor includes the first flexible wall and the rigid first container wall,
   a portion of the first flexible wall is separated away from the rigid first container wall a first distance when a first volume of urine is disposed within the collection container,
   the portion of the first flexible wall is separated away from the rigid first container wall a second distance when a second volume of urine is disposed within the collection container, and
   the second distance is different than the first distance.

5. The medical device of claim 4, wherein the rigid first container wall is a vertical wall.

6. The medical device of claim 4, wherein:
   the urine volume sensor comprises a capacitive sensor coupled with the rigid first container wall,
   the capacitive sensor is configured to detect a capacitance of a space extending between the rigid first container wall and the first flexible wall,
   the capacitive sensor detects a first capacitance when the first flexible wall is separated from the rigid first container wall the first distance, the capacitive sensor providing a first capacitance signal to the console in accordance with the first volume, and
   the capacitive sensor detects a second capacitance when the first flexible wall is separated from the rigid first container wall the second distance, the capacitive sensor providing a second capacitance signal to the console in accordance with the second volume.

7. The medical device of claim 6, wherein:
   the urine volume sensor includes a second flexible wall extending along an inside surface of a second container wall opposite the rigid first container wall,
   a portion of the second flexible wall is separated away from the portion of the first flexible wall a first separation distance when the first volume of urine is disposed within the collection container, the urine disposed between the first flexible wall and the second flexible wall,
   the portion of the second flexible wall is separated away from the portion of the first flexible wall a second separation distance when the second volume of urine is disposed within the collection container, and
   the second separation distance is different from the first separation distance.

8. The medical device of claim 7, wherein:
   the capacitive sensor is configured to detect a fluid capacitance of a space extending between the rigid first container wall and the second container wall,
   the capacitive sensor detects a third capacitance when the second flexible wall is separated from the first flexible wall the first separation distance, the capacitive sensor providing a third capacitance signal to the console in accordance with the first volume, and
   the capacitive sensor detects a fourth capacitance when the second flexible wall is separated from the first flexible wall the second separation distance, the capacitive sensor providing a fourth capacitance signal to the console in accordance with the second volume.

9. The medical device of claim 1, further including a support structure coupled with the urine receiving device, the support structure configured to facilitate hands-free use of the medical device.

10. The medical device of claim 9, wherein the support structure comprises a seat.

11. The medical device of claim 9, wherein the support structure is adjustable in height.

12. The medical device of claim 1, wherein the collection container is configured for attachment to a leg of the patient.

13. The medical device of claim 1, wherein the urine receiving device is an external female catheter configured for securement via female anatomy.

14. The medical device of claim 1, wherein the rigid first flexible wall and the first container wall extend from a top end to a bottom end of the collection container.

15. The medical device of claim 7, wherein the second container wall is disposed parallel with the rigid first container wall.

* * * * *